US012788583B2

(12) United States Patent
Gupta et al.

(10) Patent No.: US 12,788,583 B2
(45) Date of Patent: Nov. 10, 2026

(54) EXPANDABLE INTERVERTEBRAL INTERBODY IMPLANTS

(71) Applicant: GLOBUS MEDICAL, INC., Audubon, PA (US)

(72) Inventors: Munish Gupta, Frontenac, MO (US); Colm McLaughlin, Glenside, PA (US); Matthew Andraka, Conshohocken, PA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 19/332,382

(22) Filed: Sep. 18, 2025

(65) Prior Publication Data

US 2026/0000522 A1 Jan. 1, 2026

Related U.S. Application Data

(63) Continuation of application No. 18/393,932, filed on Dec. 22, 2023, now Pat. No. 12,427,038, which is a continuation-in-part of application No. 18/341,806, filed on Jun. 27, 2023, now Pat. No. 12,465,498.

(51) Int. Cl.
*A61F 2/44* (2006.01)
*A61F 2/46* (2006.01)

(52) U.S. Cl.
CPC ............ *A61F 2/447* (2013.01); *A61F 2/4611* (2013.01); *A61F 2230/0082* (2013.01); *A61F 2250/0008* (2013.01)

(58) Field of Classification Search
CPC ...... A61F 2/4611; A61F 2/442; A61F 2/4425; A61F 2/446; A61F 2002/443; A61B 34/30
USPC ........................................... 623/17.11–17.16
See application file for complete search history.

(56) References Cited

U.S. PATENT DOCUMENTS 12,427,038 B2 * 9/2025 Gupta .................... A61F 2/4455
12,465,498 B2 * 11/2025 Gupta ...................... A61F 2/442

FOREIGN PATENT DOCUMENTS

JP 2010521242 A 6/2010
JP 2013523406 A 6/2013

* cited by examiner

*Primary Examiner* — Eduardo C Robert
*Assistant Examiner* — Christina Negrellirodriguez

(57) ABSTRACT

Expandable fusion devices, systems, instruments, and methods thereof. The expandable fusion implant may include an upper endplate and a lower endplate configured to engage adjacent vertebrae, an expansion gear configured to adjust a height of the upper endplate, a locking collar configured to attach to an inserter instrument at multiple orientations for a desired surgical approach, and an actuation ram configured to lock, unlock, or change insertion orientation of the locking collar. The expandable fusion device is attachable to the inserter instrument to reorient the locking collar and expand the upper endplate.

20 Claims, 23 Drawing Sheets

EXPANDABLE INTERVERTEBRAL INTERBODY IMPLANTS

CROSS-REFERENCE TO RELATED APPLICATION

This application is a continuation of U.S. patent application Ser. No. 18/393,932 filed on Dec. 22, 2023, which is a continuation-in-part of U.S. patent application Ser. No. 18/341,810 filed on Jun. 27, 2023, which is incorporated by reference herein in its entirety for all purposes.

FIELD OF THE INVENTION

The present disclosure relates to surgical devices, and more particularly, to expandable fusion devices capable of being deployed inside an intervertebral disc space and then expanded in height to maintain disc spacing, restore spinal stability, and/or facilitate an intervertebral fusion.

BACKGROUND OF THE INVENTION

A common procedure for handling pain associated with intervertebral discs that become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of fusion devices and methodologies for accomplishing the intervertebral fusion. These may include solid bone implants, fusion devices which include a cage or other implant mechanism, which may be packed with bone and/or bone growth inducing substances, and expandable implants. The implants may be installed between adjacent vertebral bodies in order to fuse the vertebral bodies together, thereby alleviating the associated pain and providing disc height restoration.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of the interbody device to restore normal anterior column alignment. Iatrogenic pathologies may result from the surgical access window to the disc space, failure to precisely place the interbody on hard cortical bone often found on the apophyseal ring of the vertebral body, and/or failure to precisely control and restore normal anatomical spinal alignment.

As such, there exists a need for a fusion device capable of being inserted into the intervertebral disc space at a collapsed height and then expand axially to restore height loss in the disc space and further provides precise placement of the interbody, which may be inserted from multiple approaches to allow access to the spine without the need for an extensive set of implants with fixed approach-specific insertion features.

SUMMARY OF THE INVENTION

To meet this and other needs, and in view of its purposes, the present application provides devices, systems, instruments, and methods for installing and expanding an implant. In particular, an expandable fusion device is provided, which can be inserted from any approach which allows access to the spine. The expandable fusion device may have the ability to adjust the orientation of attachment to the implant to accommodate various approaches, an internal automatic lock that both provides discrete orientation positions about the central axis of the implant and automatically locks the device after insertion into the disc space, and/or has the ability to expand in height when implanted to achieve a desired spacer height which in turn provides a desired disc height.

According to one embodiment, an expandable implant includes an upper endplate and a lower endplate configured to engage adjacent vertebrae, an actuation gear configured to adjust a height of the upper endplate, the actuation gear is coupled to the lower endplate and engaged with the upper endplate, an interface collar configured to attach to an inserter instrument at multiple orientations for a desired surgical approach, the interface collar includes a plurality of angled protrusions, and an expansion and orientation lock configured to lock the orientation of the interface collar and lock the height of the upper endplate, the lock is retained in the lower endplate, the lock includes a tapered outer surface with a plurality of cuts defined therein configured to interface with the plurality of angled protrusions in the interface collar.

The expandable implant may include one or more of the following features. The interface collar may be free to rotate about a center axis of the implant when not engaged by the inserter instrument or engaged in the open position. The interface collar may be a split ring with a gap between opposite sides of the split ring. The interface collar may include a pair of eyelets defining a pair openings through the interface collar. The lower endplate may include a plurality of snap-fit posts arranged in pairs defining a space therebetween, and the lock may include a plurality of guide rail posts configured to fit into the spaces between the snap-fit posts, thereby guiding movement of the lock. The tops of the guide rail posts may protrude upward from the lock and are configured to interface with pockets on an underside of the actuation gear in order to bind rotational movement of the actuation gear and prevent expanding and collapsing of the implant. The lock may include a plurality of spring arms extending from a bottom surface of the lock, wherein in an unengaged state, the spring arms press the lock up and away from the bottom endplate. The actuation gear may include a disk with a plurality of teeth projecting radially outward therefrom and a threaded central opening configured to threadedly mate with the upper endplate. The upper endplate may include an annular body with a bone-engaging surface and an inferiorly protruding cylinder configured to mate with the actuation gear. The inferiorly protruding cylinder of the upper endplate may include exterior threads and a vertical slot bisecting the exterior threads, and the lower endplate may include a pillar receivable in the vertical slot.

According to one embodiment, an implantable system includes an expandable implant and an inserter instrument. The expandable implant includes an upper endplate configured to engage a superior vertebra, an actuation gear configured to adjust a height of the upper endplate, an interface collar configured to rotate about a center axis of the implant for a desired surgical approach, an expansion and orientation lock configured to lock the orientation of the interface collar and lock the height of the upper endplate, and a lower endplate configured to engage an inferior vertebra. The inserter instrument has an attachment assembly configured to engage the interface collar and an expansion assembly configured to expand the implant. The inserter instrument is attachable to the interface collar in an open position, a half position, and a full position to control a location of the interface collar and expansion of the implant.

The implantable system may include one or more of the following features. The attachment assembly may include an attachment fork with a pair of prongs. The interface collar may include a pair of openings configured to receive the prongs of the attachment fork. In the open position, the inserter instrument is attached to the implant such that the attachment fork is not engaged with the interface collar, thereby allowing full rotation of the interface collar and the lock prevents expansion of the upper endplate. In the half position, the inserter instrument is attached to the implant such that the attachment fork is engaged with the interface collar, thereby securing the location of the interface collar and the lock prevents expansion of the upper endplate. In the full position, the inserter instrument is attached to the implant such that the attachment fork is engaged with the interface collar, thereby securing the location of the interface collar and the lock disengages from the actuation gear allowing for expansion of the upper endplate.

According to another embodiment, a method of installing an expandable implant includes: (a) providing an expandable implant comprising an upper endplate configured to engage a superior vertebra, an actuation gear configured to adjust a height of the upper endplate, an interface collar configured to rotate about a center axis of the implant for a desired surgical approach, an expansion and orientation lock configured to lock the orientation of the interface collar and lock the height of the upper endplate, and a lower endplate configured to engage an inferior vertebra; and (b) attaching an inserter instrument to the interface collar, wherein the inserter instrument is configured to move the interface collar to an open position allowing for full rotation of the interface collar and the lock prevents expansion of the upper endplate, a half position locking a location of the interface collar and the lock prevents expansion of the upper endplate, or a full position locking a location of the interface collar and the lock disengages from the actuation gear allowing for expansion of the upper endplate. The inserter instrument may be attached to the interface collar to establish a desired trajectory including direct anterior, direct lateral, or a non-specified oblique approach between direct anterior and direct lateral. When the inserter instrument moves the interface collar to the half or full position, locking the location of the interface collar, the expandable implant may be positioned into a disc space in a collapsed position. When the inserter instrument moves the interface collar to the full position, the lock disengages from the actuation, and the actuation gear may be rotated to adjust the height of the upper endplate.

According to one embodiment, an expandable implant includes an upper endplate and a lower endplate configured to engage adjacent vertebrae, an expansion gear configured to adjust a height of the upper endplate, the expansion gear is coupled to the lower endplate and engaged with the upper endplate, a locking collar positioned between the expansion gear and the lower endplate and configured to attach to an inserter instrument at multiple orientations for a desired surgical approach, a spring received in a recess in the locking collar, and an actuation ram housed in the locking collar configured to lock, unlock, or change insertion orientation of the locking collar.

The expandable implant may include one or more of the following features. In a first position, the locking collar may be locked against the lower endplate and the expansion gear, thereby fully locking the implant. In a second position, the locking collar may be permitted to freely spin about the lower endplate for the desired surgical approach. In a third position, the locking collar may lock against the lower endplate and translate away from the expansion gear, thereby allowing for expansion of the upper endplate. The lower endplate may include a ring of teeth configured to interface with corresponding mating surfaces in the locking collar. The spring may include an elongated tab with a curved central section, which deforms under pressure. The actuation ram may include a body with two enlarged ends with a narrowed middle section. The spring may be located opposite to the actuation ram. The expansion gear may include a disk with a plurality of teeth projecting radially outward therefrom and a threaded central opening configured to threadedly mate with the upper endplate. The locking collar may include a pair of vertically projecting beams each having an inner-facing surface configured to engage with the teeth of the expansion gear. The upper endplate may include an annular body with a bone-engaging surface and an inferiorly protruding cylinder configured to mate with the expansion gear. The inferiorly protruding cylinder of the upper endplate may include exterior threads and a vertical slot bisecting the exterior threads, and the lower endplate may include a pillar receivable in the vertical slot.

According to one embodiment, an implantable system includes an expandable implant and an inserter instrument. The expandable implant includes an upper endplate configured to engage a superior vertebra, a lower endplate configured to engage an inferior vertebra, an expansion gear configured to adjust a height of the upper endplate, a locking collar configured to rotate about the lower endplate for a desired surgical approach, a spring for biasing the locking collar toward or away from the lower endplate and the expansion gear, and an actuation ram housed in the locking collar configured to lock, unlock, or change insertion orientation of the locking collar. The inserter instrument has an attachment assembly configured to engage the locking collar and an expansion assembly configured to expand the implant. The inserter instrument is attachable to the locking collar in a first position for locking the implant, a second position permitting the locking collar to freely spin for the desired surgical approach, and a third position allowing for expansion of the upper endplate.

The implantable system may include one or more of the following features. The locking collar may include a central opening, which is internally threaded, and a pair of openings positioned on opposite sides of the central opening, which are non-threaded. The actuation ram may be located inside a pocket in the locking collar. The actuation ram may include a body with two enlarged ends and a narrowed middle section. The enlarged ends may be aligned with the non-threaded openings and the narrowed middle section may be aligned with the central opening. The narrowed middle section may define a notch partially aligned with the central threaded opening. The inserter instrument may include a central threaded shaft configured to engage the central threaded opening, and a pair of non-threaded shafts configured to engage the pair of non-threaded openings. In the first position, the inserter instrument may be attached to the implant such that the inserter is not threaded into the locking collar, the spring biases the locking collar against the lower endplate and the expansion gear, thereby fully locking the implant. In the second position, the inserter instrument may be attached to the implant such that the inserter is threaded into the locking collar to a pre-determined position, the non-threaded shafts push against the actuation ram, and the locking collar releases from the lower endplate, thereby permitting the locking collar to freely spin for the desired surgical approach. In the third position, the inserter instrument may be attached to the implant such that the inserter is fully threaded into the locking collar, the non-threaded shafts push against the actuation ram overpowering the spring, and the locking collar releases the expansion gear, thereby allowing for expansion of the upper endplate.

According to another embodiment, a method of installing an expandable implant includes: (a) providing an expandable implant having an upper endplate, a lower endplate, an expansion gear configured to adjust a height of the upper endplate, a locking collar configured to rotate about the lower endplate for a desired surgical approach, a spring for biasing the locking collar toward or away from the lower endplate and the expansion gear, and an actuation ram housed in the locking collar configured to lock, unlock, or change insertion orientation of the locking collar; (b) attaching an inserter instrument to the expandable implant; (c) controlling the position and orientation of the locking collar through the inserter instrument to determine a desired trajectory; (d) inserting the expandable implant in a collapsed position between adjacent vertebrae along the desired trajectory; and (e) expanding the expandable implant through the inserter instrument. In an unengaged state, the implant may be locked such that the locking collar and the expansion gear are fully locked. The desired trajectory may be selected from direct anterior, direct lateral, or a non-specified oblique approach between direct anterior and direct lateral.

Also provided are kits including expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

In order to restore height loss in the disc space and provide precise placement of the interbody, the expandable implant may have the ability to: (1) adjust the orientation of attachment to the implant to accommodate various surgical approaches; (2) an internal automatic lock that both provides discrete orientation positions about the central axis of the implant and automatically locks the device after insertion into the disc space; and (3) the ability to expand in height when implanted to achieve a desired spacer height which in turn provides a desired disc height. Accordingly, embodiments of the present application are generally directed to devices, systems, instruments, and methods for installing and expanding the interbody implant. The terms implant, interbody, interbody implant, fusion device, spacer, and expandable device may be used interchangeably herein. Although described with reference to an interbody implant, it will be appreciated that the implant may also be used as a corpectomy spacer and placed between non-adjacent vertebral bodies or may be used in trauma or other suitable surgical applications.

The expandable interbody spacers may be inserted from any approach which allows access to the spine. The expandable spacer may be inserted into the intervertebral disc space at a collapsed height and then expand axially to restore height loss in the disc space. The expandable interbody spacers may be configured to maximize volume within and around the device for graft material. Alternatively, the spacers may be used as a corpectomy spacer, which is placed between non-adjacent vertebral bodies. The spacers may be provided in various footprints and profiles with superior and inferior geometry that when implanted will be in contact with the boney surfaces of the vertebral bodies the spacer is implanted between. The superior and inferior geometry may be provided angled as to accommodate wide ranging anatomical profiles and to match or restore lordosis when used in the lumbar spine, for example.

Figure 1A:
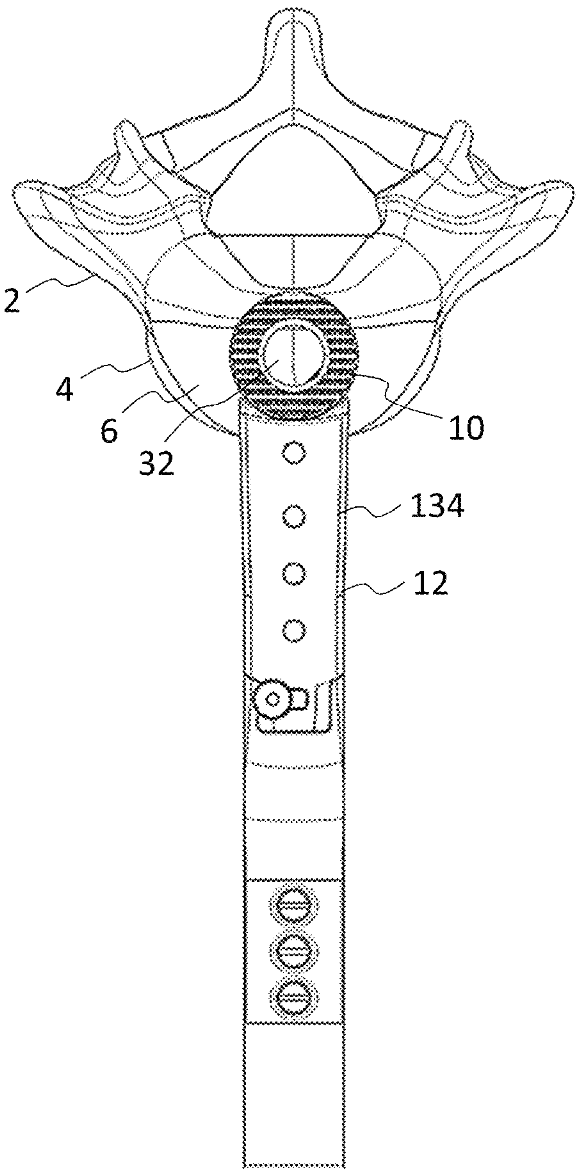
FIGS. 1A-1C show an inserter instrument attached to an expandable implant for a direct anterior approach, non-specified oblique approach, and direct lateral approach, respectively, according to one embodiment.
Figure 1B:
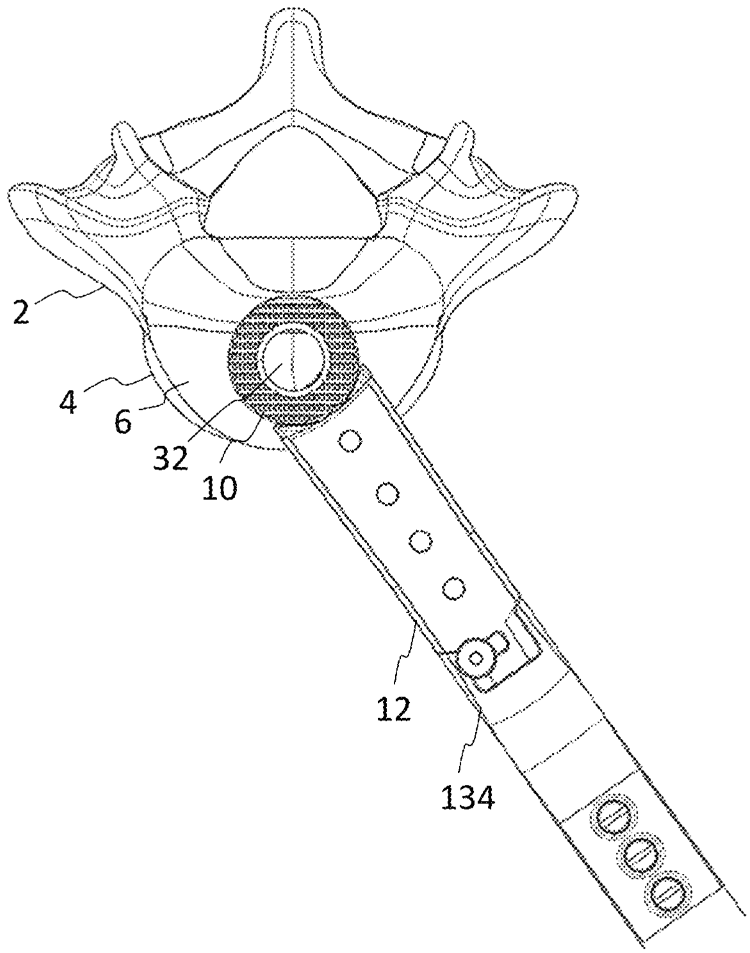
Figure 1C:
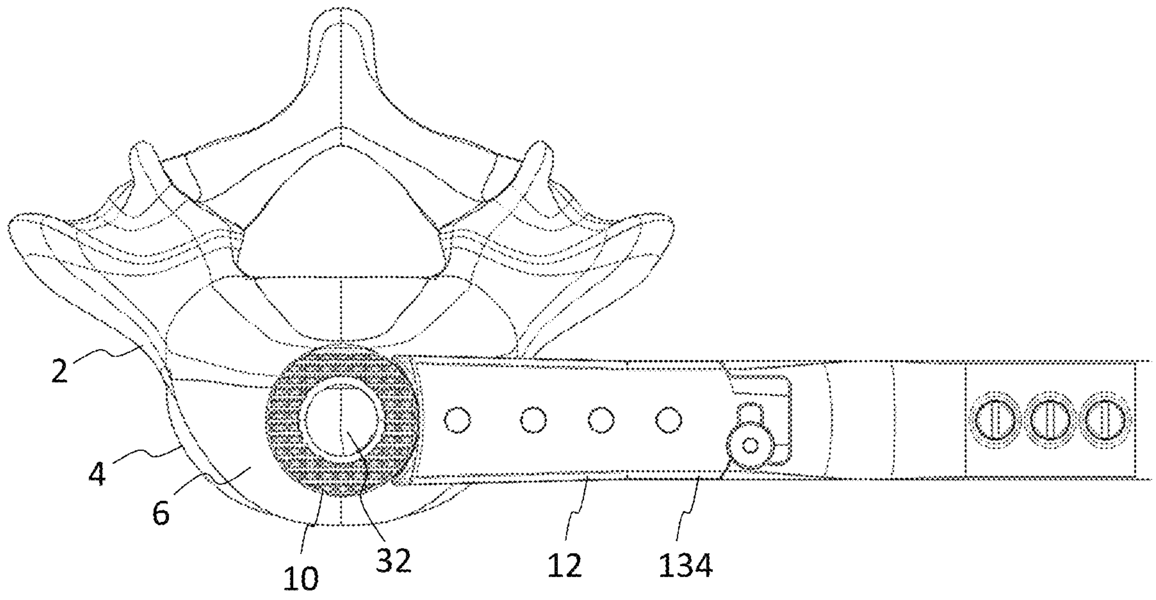

Turning now to the drawing, where like reference numerals refer to like elements, FIGS. 1A-1C show an expandable interbody fusion device or implant 10 and methods of installation according to one embodiment. The expandable device 10 is configured to be inserted between two adjacent vertebrae 2. The expandable implant 10 is attached to an inserter instrument 12 to deploy the device 10 into the disc space (the upper vertebra is omitted for clarity in FIGS. 1A-1C). The inserter 12 may be suitable for use during a minimally invasive surgical (MIS) procedure, for example, such that the inserter 12 and attached implant 10 may be positioned through a guide tube or cannula to access and guide the implant 10 into the disc space. The expandable implant 10 is inserted between the vertebral bodies 4 of the vertebrae 2 and into the disc space in a collapsed position.

The implant 10 is configured to adjust the orientation of attachment of the inserter 12 relative to the implant 10 to accommodate various surgical approaches to the spine. The ability to adjust the implantation orientation of the implant 10 accommodates a variety of approach angles and trajectories to the spine. The surgical approach angles and trajectories may include direct anterior, direct lateral, oblique, and subdivided increments in-between direct anterior and direct lateral. FIG. 1A shows placement of implant 10 through a direct anterior approach to the spine from the front of the body. When operating on the lumbar spine, this surgical technique may also be called an anterior lumbar interbody fusion (ALIF). FIG. 1B shows placement of implant 10 through a non-specified oblique approach (e.g., at an angle between direct anterior and direct lateral). FIG. 1C shows placement of implant 10 through a direct lateral approach to the spine from a side of the body. When operating on the lumbar spine, this surgical technique may also be called a lateral lumbar interbody fusion (LLIF). It will be appreciated that the surgeon may determine the best surgical approach and placement of the expandable implant 10 before or during the surgery.

Once inserted into the disc space through the desired surgical approach, the implant 10 is then expanded in height to an expanded position to precisely restore normal spinal alignment and distribute the load across the vertebral endplates 6. Due to the adjustable attachment interface, the implant 10 may be oriented or angled to better contact the natural endplate curvature of the vertebral bodies 4 above and below the disc space in which the device 10 is being implanted. This may be especially beneficial in high-complexity deformity cases where vertebral bodies 4 may be rotated relative to more than one dimensional plane, thus requiring a non-typical surgical access approach to the level the surgeon desires to treat.

Figure 2:
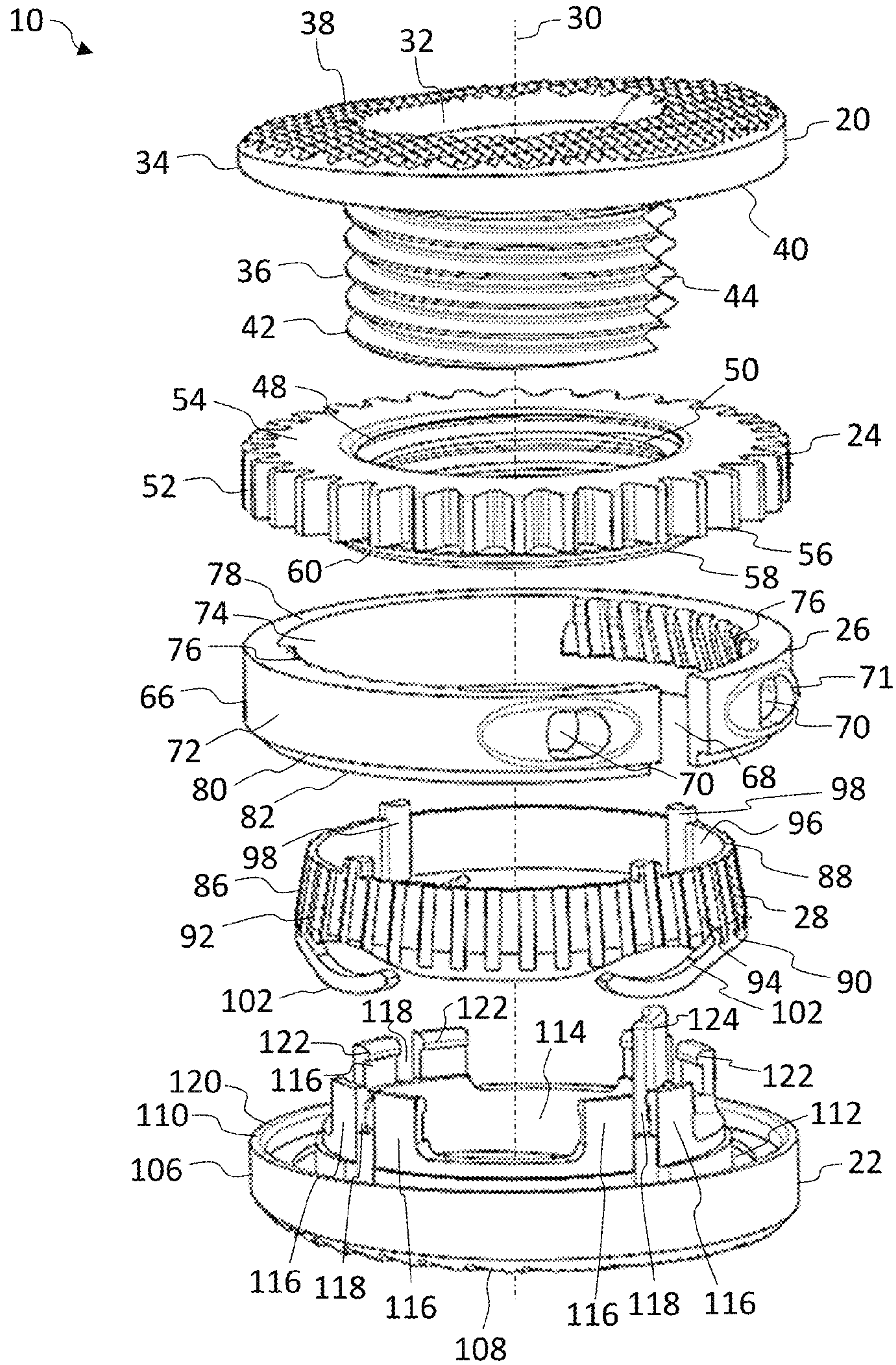
FIG. 2 is an exploded view of the expandable implant according to one embodiment.
Figure 5:
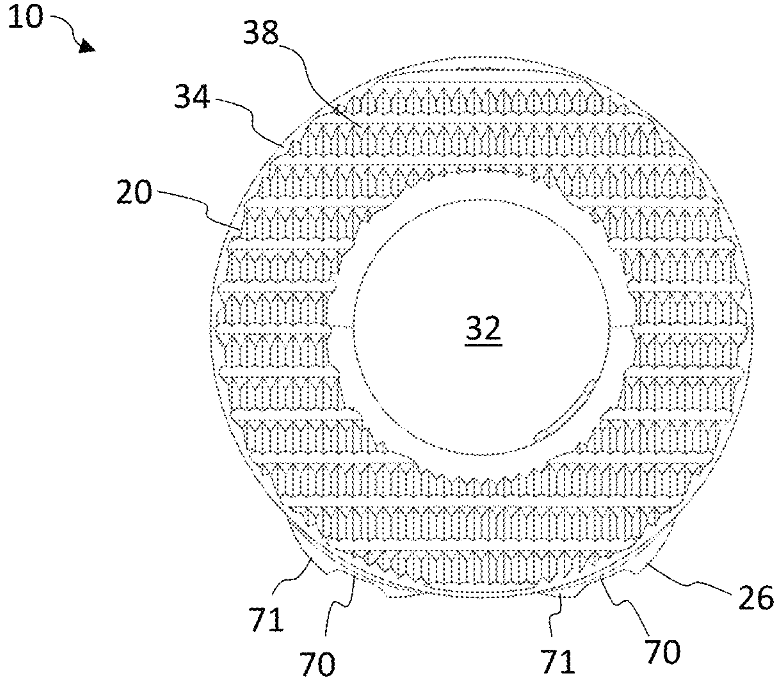
FIG. 5 shows a top view of the expandable fusion device of FIG. 2.

Turning now to FIG. 2, an exploded view of expandable implant 10 is shown according to one embodiment. The implant 10 includes an upper endplate 20 for engaging a superior vertebral body 4, a lower endplate 22 for engaging an inferior vertebral body 4, an expansion or actuation gear 24 for adjusting the height of the upper endplate 20, an orientation and interface collar 26 configured to attach the inserter 12 to the implant 10 at various orientations or angles for the desired surgical approach angle or trajectory, and an expansion and orientation lock 28 configured to lock the orientation of the interface collar 26 and/or automatically lock the height of the implant. The endplates 20, 22, actuation gear 24, interface collar 26, and lock 28 are aligned along central longitudinal axis 30. The implant 10 may define a large central graft retaining opening or window 32 configured to receive bone graft or other suitable bone growth enhancing material. As best seen in FIG. 5, the central graft window 32 may be generally cylindrical in shape with a central axis aligned with central longitudinal axis 30.

The top or upper endplate 20 includes an annular body 34 with an inferiorly protruding cylinder 36 configured to mate with the actuation gear 24. The annular body 34 may be a ring or circle surrounding a portion of the central graft window 32. The annular body 34 has a thickness between an upper bone-engaging surface 38 and a bottom or lower surface 40 of annular body 34. As best seen in FIGS. 3A-3B and 4A-4B, the annular body 34 may be angled and/or the thickness between the upper and lower surfaces 38, 40 of the annular body 34 may vary to accommodate wide ranging anatomical profiles and to match or restore lordosis when used in the lumbar spine.

The annular body 34 includes upper bone-engaging surface 38 configured to engage a superior vertebral body 4. The upper bone-engaging surface 38 may be contoured to mimic the shape of the vertebral endplate 6. The upper bone-engaging surface 38 may include a plurality of teeth, protrusions, or other friction enhancing surfaces configured to engage bone. In one embodiment, the upper endplate 20 includes aggregate-like expulsion resistant patterns or textures on the superior surface geometry for contacting bony surfaces that can be angled to match or restore lordosis when used in the lumbar spine. The bony-contacting surface 38 may further include a porosity or porous structure to allow for additional ingrowth of bone into the spacer. The upper endplate 20 may be 3D printed, for example, to enhance boney on-growth potential. It will be appreciated that the bone-engaging surface 38 may be modified to include one or more surface treatments, coatings, textures, or other features to enhance fusion.

Cylinder 36 extends from the bottom or lower surface 40 of annular body 34. The protruding cylinder 36 defines one or more exterior threads 42 configured to mate with corresponding threads 50 inside the actuation gear 24. The exterior threads 42 may include a helical thread profile machined into the outer surface of the cylinder 36. The exterior threads 42 may have any suitable attributes including diameters, handedness, thread form, thread angle, lead (s), pitch, etc. The threads 42 may extend along the entire length of cylinder 36 or a suitable portion thereof. As the cylinder 36 is telescopingly received in/from the actuation gear 24, the upper endplate 20 is configured to raise or lower in height, thereby adjusting the overall height of the implant 10. A slot 44 may run the full length or partial length of the threads 42 and reaches into the central graft window 32. The slot 44 may be vertically oriented and in fluid communication with the central graft window 32. The slot 44 may be located at an angle from direct anterior to allow for access from various approach angles. The slot 44 may act as a backfill window and a counter-torque for expansion and collapsing of the spacer.

The expansion gear or actuation gear 24 is configured to expand and collapse the implant 10. The actuation gear 24 has a central through opening 48 sized and dimensioned to receive the protruding cylinder 36 of the upper endplate 20 in a telescoping manner. The central opening 48 has a center axis coaxial with the central longitudinal axis 30 of the implant 10. The central opening 48 defines one or more inner threads 50 cut into its inner diameter configured to interface with the exterior threads 42 of the upper endplate 20. The threaded engagement between the cylinder 36 and threaded opening 48 permit the actuation gear 24 to adjust the height of upper endplate 20 when rotated.

An outer perimeter of the actuation gear 24 includes a plurality of cogs or teeth 52. In one embodiment, the actuation gear 24 may be a spur gear or straight-cut gear with straight teeth 52 projecting radially from the cylinder or disk. The edge of each tooth 52 may be straight and aligned parallel to the axis of rotation. Although a specific arrangement of teeth 52 is shown, it is envisioned that the number, location, thickness, diameters, pitch, and configuration of the teeth may be modified or selected by one skilled in the art. When engaged by inserter instrument 12, the actuation gear 24 may be rotated about axis 30 to move upper endplate 20 up or down, thereby adjusting the height of the implant 10.

Figure 3A:
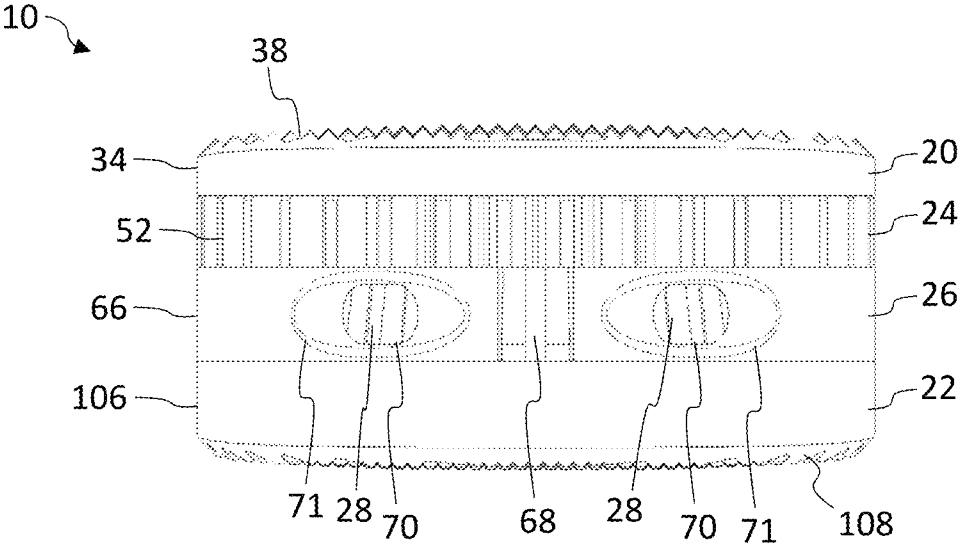
FIGS. 3A-3B show front and left side views, respectively, of the expandable fusion device of FIG. 2 at the collapsed starting height.
Figure 3B:
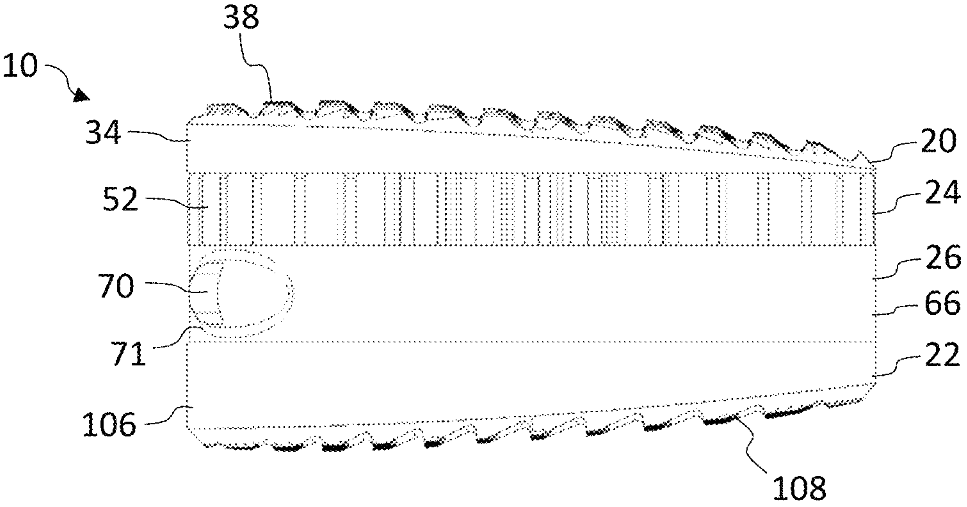

The teeth 52 may extend between an upper face 54 and an opposite lower face 56 of actuation gear 24. The upper face 54 of the actuation gear 24 may be configured to contact the bottom surface 40 of annular body 34 of the upper endplate 20 when the upper endplate 20 is fully collapsed (as shown in FIGS. 3A-3B). The lower face 56 of the actuation gear 24 is configured to contact or be adjacent to the upper surface 78 of collar 26 at all times. The upper and lower surfaces 54, 56 of the actuation gear 24 may be generally planar and smooth.

Figure 8A:
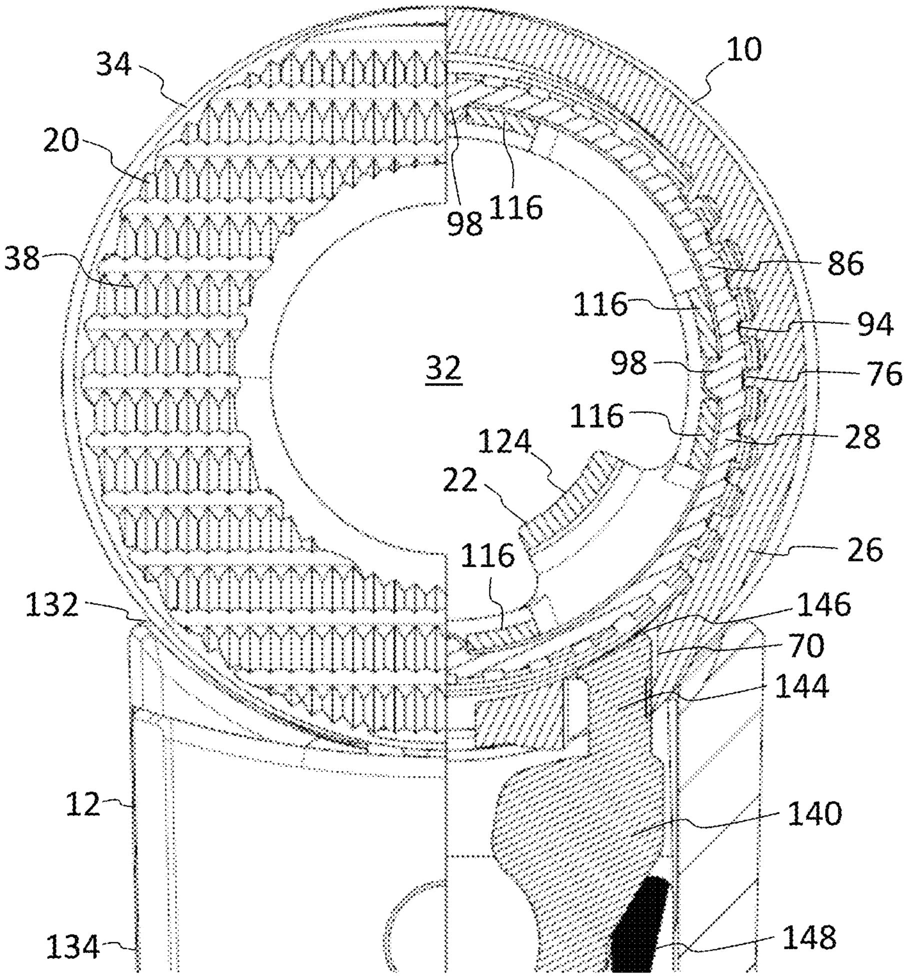
FIGS. 8A-8B show a partial top view (left side) and a partial cross-sectional view (right side) and a side cross-sectional view, respectively, of the inserter instrument located at a half locking position with the implant to lock the implantation trajectory but not unlocking the expansion gear.
Figure 8B:
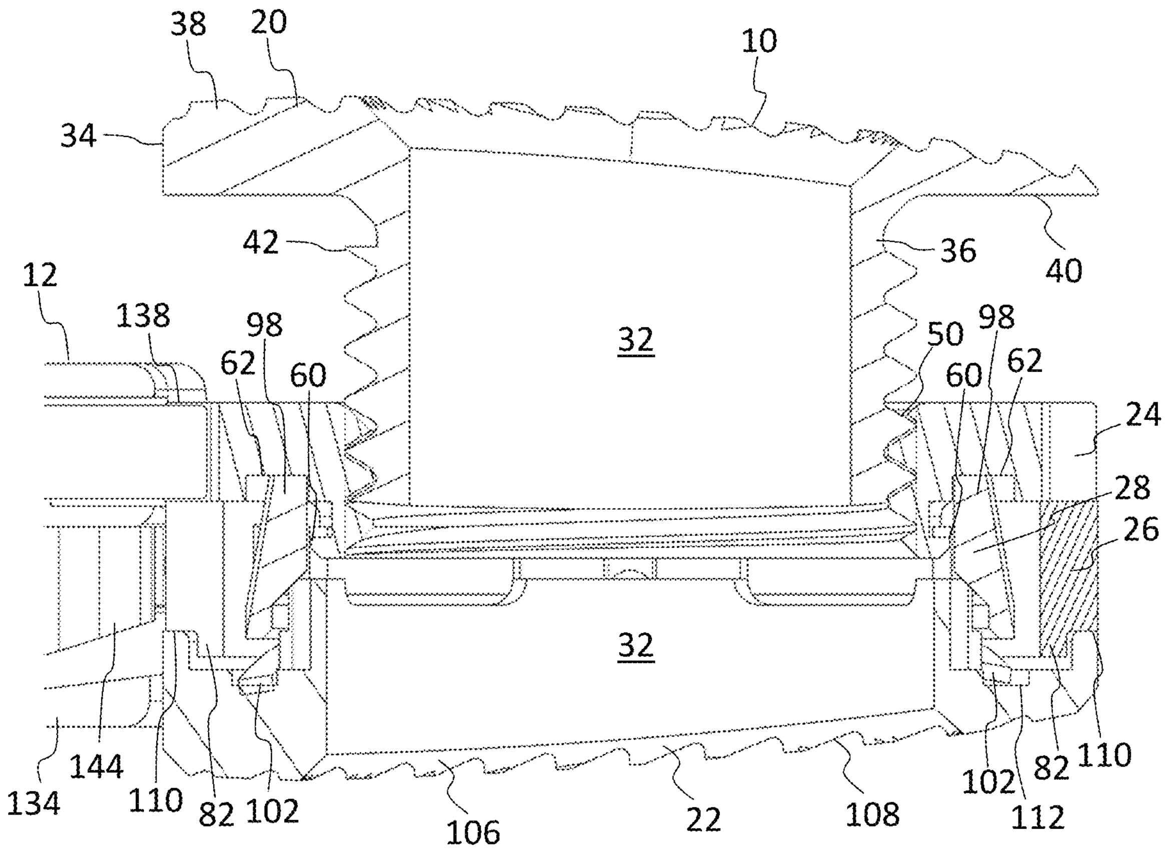

The actuation gear 24 includes a snap-fit lip 58, which protrudes inferiorly and is configured to be retained by the bottom endplate 22. As best seen in FIG. 8B, the snap-fit lip 58 may include a circular rim 60 defined by a circular groove superior to rim 60. The circular rim 60 protrudes radially outward to engage with the bottom endplate 22. A bottom portion or surface of the rim 60 may be angled or rounded to help with the snap-fit engagement. The lower surface 56 of the actuation gear 24 defines a plurality of pockets 62 configured to retain a portion of lock 28. The lock 28 is configured to interface with pockets 62 in the lower face 56 on the underside of the actuation gear 24 in order to bind the rotational movement of the expansion gear 24 and prevent both expansion and collapsing of the implant 10.

The orientation and interface collar 26 is configured to interface with the inserter 12 for implantation. When not engaged by the inserter 12, the collar 26 is permitted to freely rotate about axis 30. When engaged by the inserter 12 in certain positions, the collar 26 is locked into position relative to the inserter 12 for implantation for a desired approach or trajectory. The interface collar 26 includes a split ring body 66 with a gap 68 between opposite sides of the split ring 66. The interface collar 26 defines one or more openings 70 through the outer face 72 of the outer diameter which are configured to interface with the inserter 12 for implantation. The outer face 72 may be generally smooth except for a pair of protruding oblong eyelets 71 on opposite sides of the gap 68. Each opening 70 may be defined through the respective eyelet 71.

The inner surface 74 of the interface collar 26 includes a plurality of angled protrusions 76. The angled protrusions 76 may include a series of alternating protrusions and grooves configured to interface with corresponding mating surfaces 94 on the lock 28. The angled protrusions 76 may define flanks or ramped surfaces configured to translate the lock 28 vertically along axis 30. The angled protrusions 76 may extend from an upper face 78 a distance toward lower face 80 while stopping short of the lower face 80 allowing a smooth area below protrusions 76. In one embodiment, a first series of angled protrusions 76 extend a distance along inner surface 74 from first opening 70 and a second series of angled protrusions 76 extend a distance along inner surface 74 from the second opening 70 with a smooth area along inner surface 74 between the two series of protrusions 76. Although a specific arrangement of angled protrusions is shown, it is envisioned that the number, location, and configuration of surfaces may be modified or selected by one skilled in the art.

The rotatable interface collar 26 is located between the actuation gear 24 and the bottom endplate 22. The interface collar 26 may be retained in the bottom endplate 22 by overlapping lips 82, 120 on the collar 26 and the bottom endplate 22. The lip 82 on interface collar 26 may include a downward projecting lip following the body of the split ring 66 along the interior surface 74. It will be appreciated that the interface collar 26 may be retained in the bottom endplate 22 using any suitable mechanism that permits rotational movement of collar 26 about axis 30 when the collar 26 is not secured by the inserter 12.

The interface collar 26, when not engaged by the inserter 12, is permitted to freely rotate 360° around the central axis 30 of the implant core. The collar 26 may be engaged by inserter 12 in multiple positions. In a first position, the angled protrusions 76 of the collar 26 interface with the lock 28 to prevent the collar 26 from rotating, which locks the orientation of the implant 10 relative to the inserter 12 for implantation. In a second position, the collar 26 causes the lock 28 to disengage from the actuation gear 24, thereby allowing for expansion or collapsing of the implant 10 and also prevents rotation and reorientation of the collar 26.

The expansion and orientation lock 28 is configured to lock the orientation of the interface collar 26 and/or automatically lock the height of the implant 10. The outer diameter 92 of lock 28 is tapered with angled shallowed cuts 94, which interact and interface with mating protrusions 72 on the interface collar 26. The lock 28 includes a ring-like body 86 angled or tapered from a top edge 88 to bottom edge 90. The body 86 gradually increases in diameter along its circumference from top edge 88 to lower edge 90 forming an outer cone-like shape. Thus, the top edge 88 has a smaller diameter than bottom edge 90. The outer diameter of the lock 28 includes a plurality of shallow cuts 94. The shallow cuts 92 may be generally rectangular in shape extending vertically from upper edge 88 toward bottom edge 90. The cuts 92 may have equal widths and may be equally spaced about the perimeter of the lock 28 or may be otherwise configured to mate with corresponding protrusions 72 in the interface collar 26. The inner surface 96 of the lock 28 may be smooth.

The lock 28 has one or more guide rail posts 98 that interface with the bottom endplate 22 acting as counter-torque measure so that the lock 28 is permitted to only move in a linear fashion up and down along axis 30. Each guide rail post 98 may include a vertical rail protruding radially inwardly. For example, four guide rails posts 98 may be spaced equally about the inner surface 94 of the lock 28. It will be appreciated that any suitable number and configuration of guide rail posts may be used to guide the movement of the lock 28. The tops of the guide rail posts 98 protrude upward and are configured to interface with the pockets 62 on the underside of the actuation gear 24 in order to bind the rotational movement of the actuation gear 24 and prevent expanding and collapsing of the implant 10. The lock 28 may include one or more spring arms 102 extending from the bottom surface 90 of the lock 28 with each terminating at a free end. The spring arms 102 may include a curved beam or structure that bends downward with a convex lower profile. A spring arm 102 may be positioned beneath each guide rail post 98. Each spring arm 102 may be machined into the lock 28 such that in the implant's unengaged state, the spring arms 102 press the lock 28 up and away from the bottom endplate 22.

The lower endplate 22 includes an annular body 106 configured to receive the expansion and orientation lock 28, the interface collar 26, and the actuation gear 24. Similar to upper endplate 20, the annular body 106 may be a ring or circle surrounding a portion of central graft window 32. The annular body 106 has a thickness between a lower bone-engaging surface 108 and an upper edge 110 of annular body 34. As best seen in FIGS. 3A-3B and 4A-4B, the annular body 106 may be angled and/or the thickness between the upper and lower surfaces 108, 110 of the annular body 106 may vary to accommodate wide ranging anatomical profiles and to match or restore lordosis when used in the lumbar spine.

The lower bone-engaging surface 108 of lower endplate 22 is configured to engage an inferior vertebral body 4. The lower bone-engaging surface 108 may be contoured to mimic the shape of the vertebral endplate 6. Similar to upper bone-engaging surface 38, lower bone-engaging surface 108 may include a plurality of teeth, protrusions, or other friction enhancing surfaces configured to engage bone. In one embodiment, the bottom endplate 22 includes aggregate-like expulsion resistant patterns or textures on the inferior surface geometry for contacting bony surfaces that can be angled to match or restore lordosis when used in the lumbar spine. The lower bone-engaging surface 108 may further include a porosity or porous structure to allow for additional ingrowth of bone into the spacer. The lower endplate 22 may be 3D printed, for example, to enhance boney on-growth potential. It will be appreciated that the bone-engaging surface 108 may be modified to include one or more surface treatments, coatings, textures, expulsion resistant structures or geometries, or other features to enhance fusion.

Assembly, counter-torque, and interfacing features for the lock 28 are machined into an upper portion of the lower endplate 22. The expansion and orientation lock 28 lives nested inside of pockets and grooves 112 machined into the bottom endplate 22. The lower endplate 22 has an inner wall 114 define by a portion of central graft window 32. A plurality of snap-fit posts 116 extend vertically from the inner wall 114. The snap-fit posts 116 are arranged in pairs with a space 118 therebetween configured to receive respective guide rail posts 98 of the lock 28. In the embodiment shown, four pairs of snap-fit posts 116 are spaced equally around the inner wall 114 defining four respective spaces 118 for corresponding guide rail posts 98. The guide rail posts 98 interface with the spaces 118 between the snap-fit posts 116 to guide movement of the lock 28 in a linear fashion up and down along axis 30. Although a certain number and configuration of posts 98, 116 are shown, it will be appreciated that another suitable arrangement may be selected to guide lock 28.

After the lock 28 is positioned into lower endplate 22, the interface collar 26 is placed into lower endplate 22 such that the collar 26 surrounds and engages lock 28. The interface collar 26 may be retained in the lower endplate 22 by overlapping lips 82, 120 on the collar 26 and bottom endplate 22. The collar 26 may be sized and dimensioned such that the outer face 72 of the orientation collar 26 is generally flush with the outer circumference of the annular body 106 of the lower endplate 22.

The actuation gear 24 may then be positioned on top of the orientation collar 26 and secured to the lower endplate 22. The lower face 56 of the actuation gear 24 abuts the upper face 78 of the interface collar 26. The actuation gear 24 may be sized and dimensioned such that the outer diameter of the gear 24 is generally flush with the outer face 72 of the interface collar 26 and the outer circumference of the annular body 34 of the upper endplate 20. The lower face 56 of actuation gear 24 rests on top of the snap-fit posts 116 in the bottom endplate 22. The actuation gear 24 is retained in the bottom endplate 22 via snap-fit lip 60. Each of the free ends of snap-fit posts 116 define an overhang or finger 122 configured to fit in the groove defining circular rim 60 of actuation gear 24. The snap-fit posts 116 may be configured to flex or bend slightly as the fingers 122 are inserted, thereby securely connecting the actuation gear 24 to the lower endplate 22.

Figure 4A:
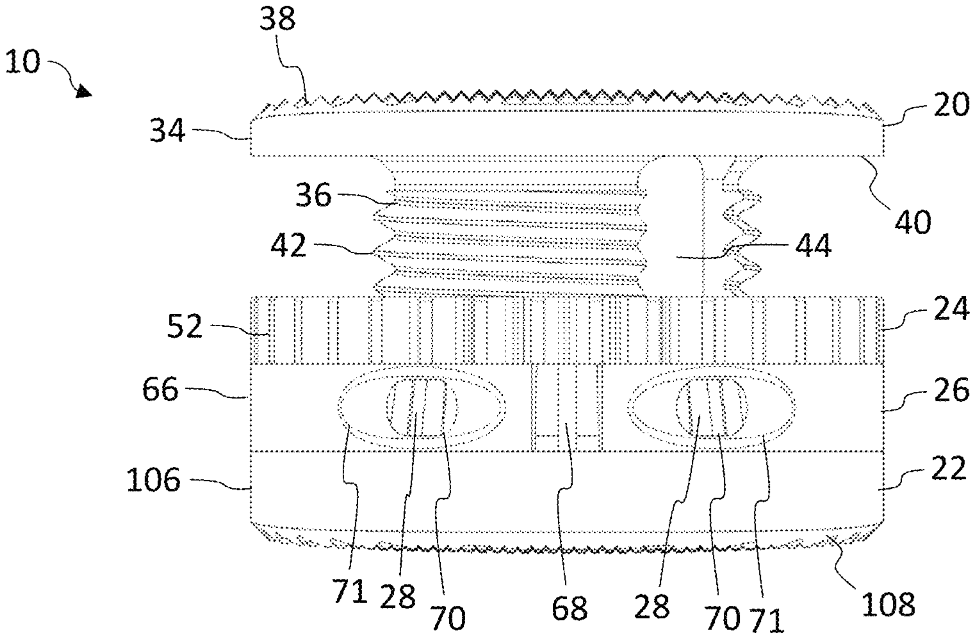
FIGS. 4A-4B show front and left views, respectively, of the expandable fusion device of FIG. 2 fully expanded in height.
Figure 4B:
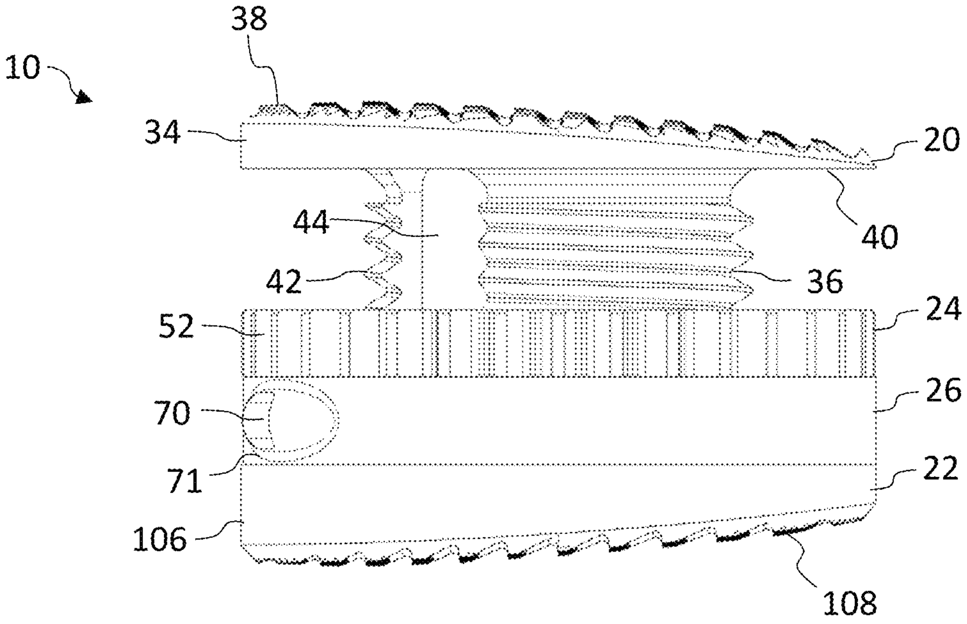

The upper endplate 20 is threadedly engaged with actuation gear 24. A pillar 124 may protrude vertically from lower endplate 22, which is sized and configured to fit within slot 44 in the cylinder 36 of the upper endplate 20. When in the fully collapsed position, the slot 44 and pillar 124 may act as a counter-torque measure for expansion and collapsing of the spacer. When the implant 10 is fully collapsed as shown in FIGS. 3A-3B, the bottom surface 40 of the annular body 34 of the upper endplate 20 may contact and abut the upper face 54 of the actuation gear 24. When the implant 10 is expanded as shown in FIGS. 4A-4B, the annular body 34 of the upper endplate 20 lifts off the actuation gear 24 and the bottom surface 40 of the annular body 34 is spaced apart from the actuation gear 24.

The devices described herein or components thereof may be manufactured from a number of biocompatible materials including, but not limited to, titanium, titanium alloys, non-titanium metallic alloys, stainless steel, polymeric materials, plastics, plastic composites, polyetheretherketone (PEEK), ceramics, and elastic materials. The devices or components thereof may be manufactured by machining, additive processes such as 3-dimensional (3D) printing, and/or subtractive processes.

Turning now to FIGS. 6A-9B, implant 10 is insertable into the disc space with inserter 12 through an agnostic approach. In other words, the surgeon is able to determine the trajectory or approach to the spine before or during the procedure and is able to adjust the orientation of the implant 10 during the procedure to accommodate the desired surgical approach. The implant 10 is configured to be inserted from multiple approaches without the need for an extensive set of implants with fixed approach-specific insertion features. The ability of implant 10 to be inserted from multiple approaches and trajectories can significantly reduce the number of necessary implants in the set list for a given procedure. The flexibility of implant 10 also provides the surgeon with more choices and greater control during the procedure, thereby resulting in better patient outcomes.

Figure 6A:
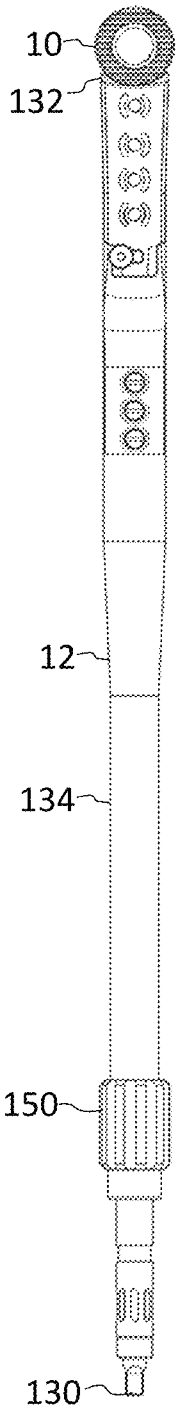
FIGS. 6A-6C show top and cross-sectional views, respectively, of the inserter instrument attached to the expandable implant according to one embodiment.
Figure 6B:
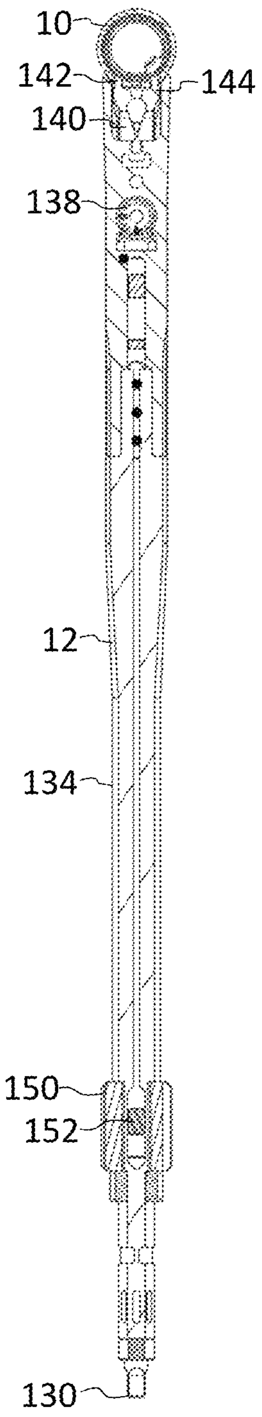
Figure 6C:
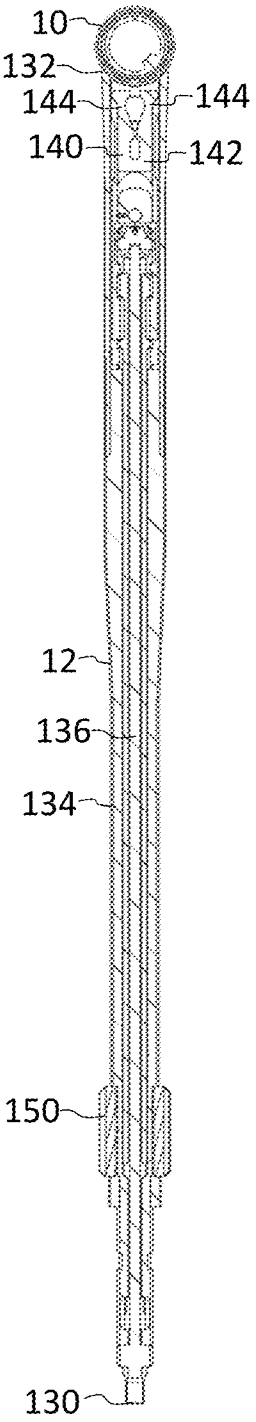

FIGS. 6A-6C show inserter instrument 12 attached to implant 10 according to one embodiment. The inserter 12 controls the position of the interface collar 26, the position of the lock 28, and the expanded height of the top endplate 20 when properly attached. The inserter 12 extends from a proximal end 130 to a distal end 132 along a central longitudinal tool axis. The proximal end 130 includes an attachment interface for connecting a handle (not shown) configured to be manipulated by a user. The distal end 132 is configured to attach to the interface collar 26 of the implant 10. The inserter 12 includes a main outer body 134 in the form of a hollow outer tube or cannula defining a central channel configured to receive an expansion assembly including an expansion drive shaft 136 configured to expand the implant 10 and an attachment assembly including a distal attachment fork 140 configured to engage the interface collar 26 in different positions.

The expansion assembly may include expansion drive shaft 136, which is a cylindrical shaft extending through outer body 134, attached to a drive gear 138 configured to engage with the actuation gear 24 of the implant 10. The proximal end 130 of expansion drive shaft 136 is connectable to a handle (not shown) to allow for rotation of the drive shaft 136. When the inserter 12 is engaged with the orientation collar 26 in a full position, turning the expansion drive shaft 136 rotates drive gear 138, which interfaces with actuation gear 24 to allow for expansion or contraction of the upper endplate 20, thereby allowing for adjustment of the height of the implant 10.

The attachment assembly may include attachment fork 140, which includes a central body or base 142 with a pair of distal prongs 144 extending therefrom. The prongs 144 may be straight or curved and may be spaced apart to match the spacing of the attachment locations 70 along the interface collar 26. The prongs 144 may be configured to flex or bend slightly to engage the interface collar 26 in different positions. The free end 146 of each prong 144 may be inserted into respective opening 70 and may be contoured or shaped to engage with opposite sides of the opening 70. A sleeve 148 may be configured to draw the prongs 144 together or apart. An outer control knob 150 and inner half nut 152 may be used to manipulate the prongs 144. For example, the control knob 150 may be rotated to translate sleeve 148 to draw prongs 144 together or allow prongs 144 to spread apart from one another. It will be appreciated that any suitable mechanism may be used to control movement of the attachment fork 140 and prongs 144.

Figure 7:
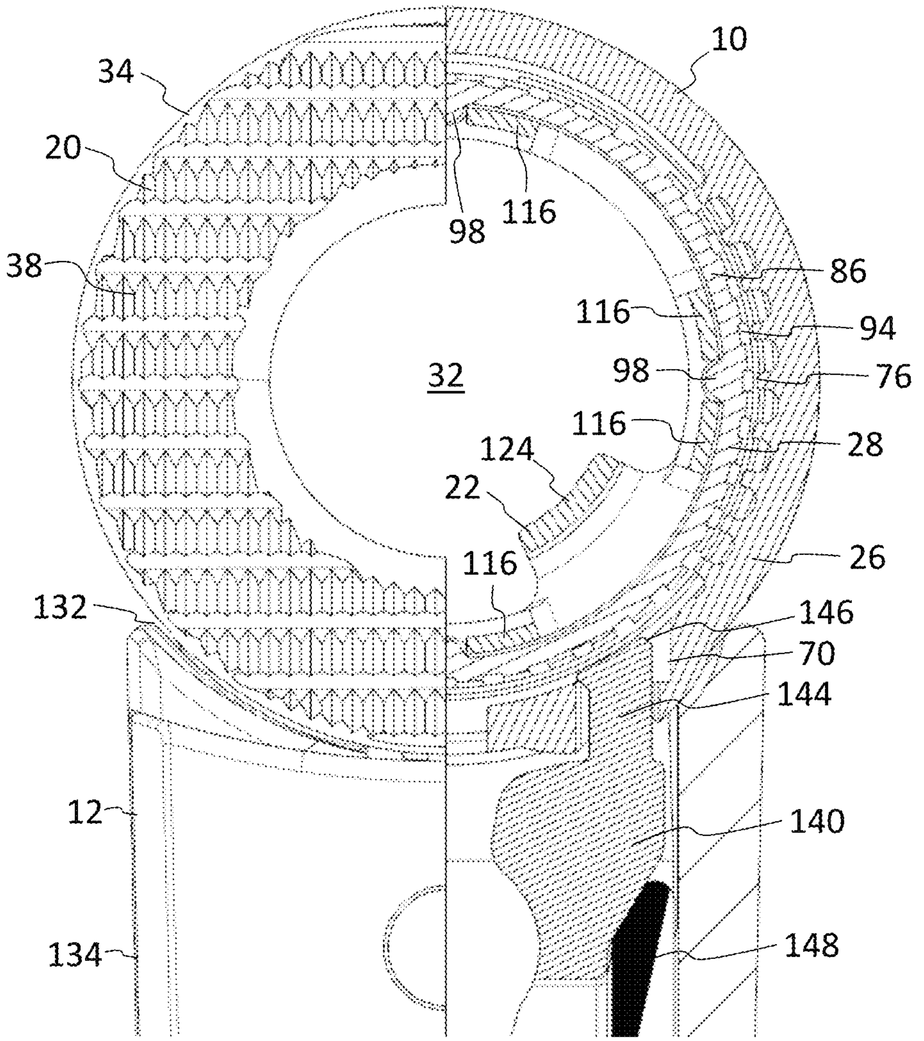
FIG. 7 shows a partial top view (left side) and a partial cross-sectional view (right side) of the inserter instrument in a neutral open position with the implant but not engaged with the interface collar.

FIG. 7 shows the inserter 12 attached to implant 10 such that the attachment fork 140 is not engaged with the interface collar 26, thereby providing a neutral or open position. When the collar 26 is not engaged by the inserter 12, the collar 26 is permitted to freely rotate 360° around the central axis 30 of the implant core. The angled protrusions 76 of the interface collar 26 are not received in the shallow cuts 94 of the lock 28. The open position occurs when the control knob 150 is twisted such that the attachment fork 138 results in a position where the prongs 144 of the fork 140 are not engaged with the attachment points 70 on the interface collar 26. FIG. 7 shows the prong 144 in a neutral position in opening 70 of the interface collar 26, thereby allowing for full rotation of the interface collar 26 to the desired insertion orientation.

When the collar 26 is engaged by the inserter 12, the angled protrusions 76 of the collar 26 interface with the angled shallow cuts 94 on the lock 28. The collar 26 may be engaged by the inserter 12 in two different positions: half position and full position. FIGS. 8A-8B show the inserter 12 attached to implant 10 at the half position. In the half position, the attachment fork 140 is engaged with the interface collar 26, and the prong 144 is located in opening 70 of the interface collar 26 such that the prongs 144 move away from one another. When engaged at the half position by inserter 12, the protrusions 76 of interface collar 26 bind with the cuts 94 on the lock 28 and prevent the collar 26 from rotating, which in turn defines the orientation of the implant 10 relative to the inserter 12 for implantation. The half position occurs when the control knob 150 is twisted such that the attachment fork 140 results in a position where the prongs 144 of the fork 140 are forcing the ramped interacting features on the interface collar 26 to engage with the lock 28. In the half position, the orientation of the interface collar 26 is rigidly defined, while not unlocking the expansion mechanism.

Figure 9A:
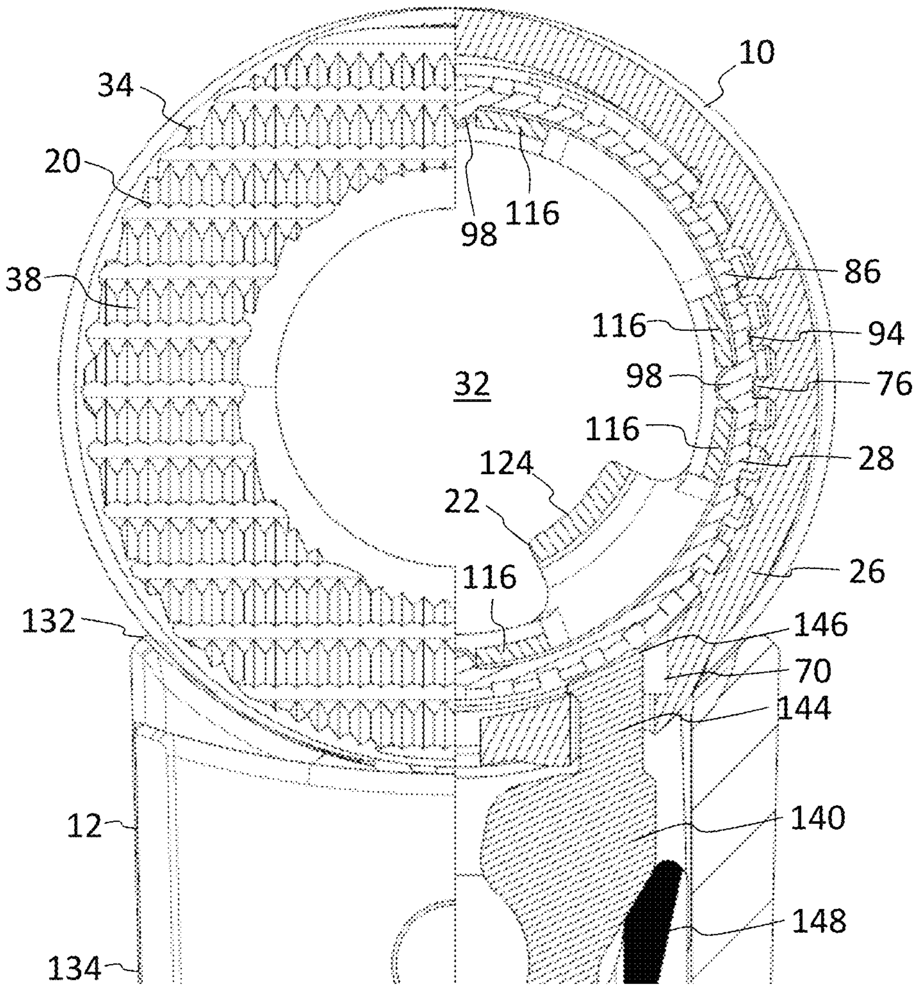
FIGS. 9A-9B show a partial top view (left side) and a partial cross-sectional view (right side) and a side cross-sectional view, respectively, of the inserter instrument located at a full locking position with the implant to lock the implantation trajectory and unlocking the expansion gear to allow for expansion or contraction of the implant.
Figure 9B:
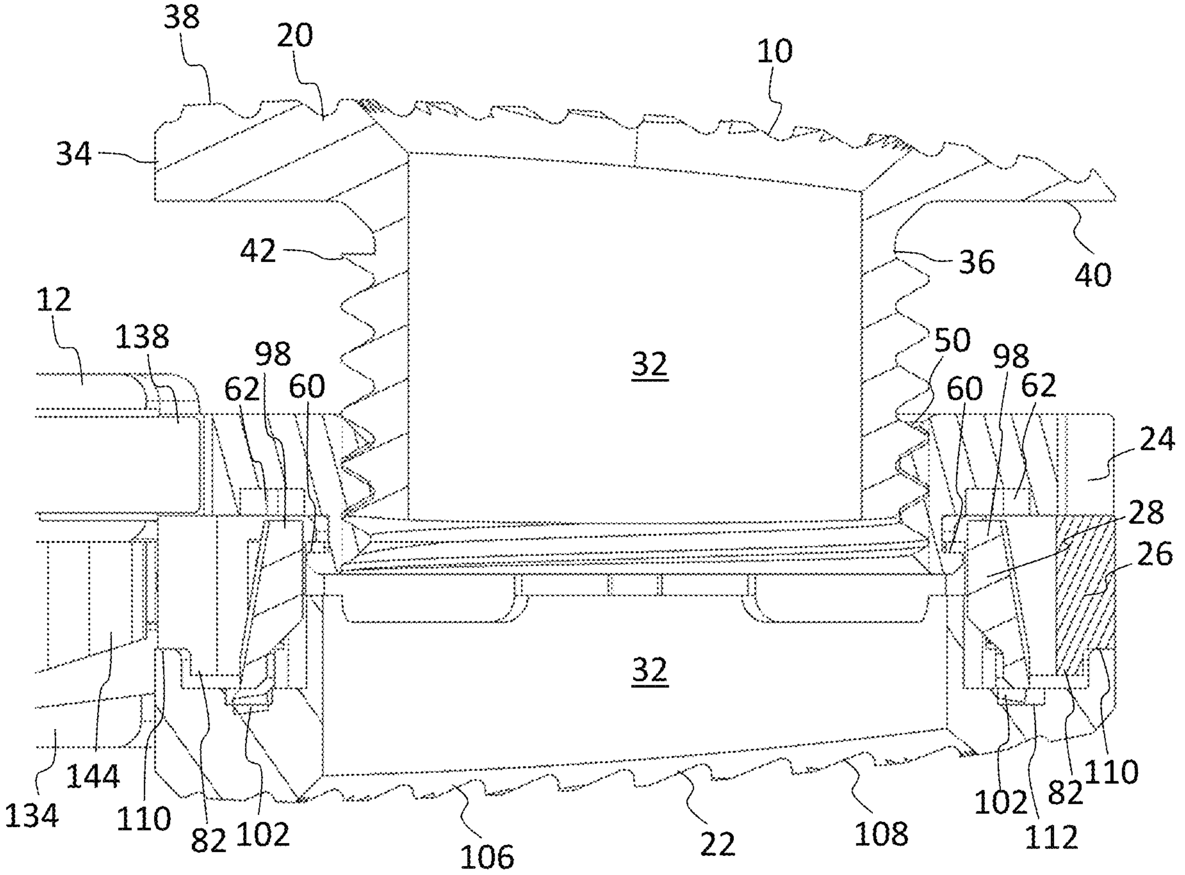

FIGS. 9A-9B show the inserter 12 attached to implant 10 at the full position. When engaged in the full position by the inserter 12, the ramped features of the interface collar 26 push into and down on the lock 28 disengaging the rail posts 98 from the underside of the gear 24 allowing for expansion or collapsing of the implant 10, as well as implantation or removal. The full position also prevents rotation and reorientation of the collar 26. In the full position, the prongs 144 of the attachment fork 144 may be drawn toward one another to grip the interface collar 26 such that the ends of split ring 66 approach one another, thereby causing the interface collar 26 to engage the lock 28. The full position occurs when the control knob 150 is twisted such that the attachment fork 140 results in a position where the prongs 144 of the fork 140 are forcing the interacting features 76 on the interface collar 26 to engage with the lock 28. In this manner, the orientation of the interface collar 26 is rigidly defined and the ramped interacting features 76 of the interface collar 26 push the lock 28 downward and away from the expansion gear 24. The upper ends of guide rail posts 98 on the lock 28 disengage from the pockets 62 in lower surface 56 of the actuation gear 24, thereby unlocking the implant 10.

Once in the full position, the upper endplate 20 may be raised or lowered. For example, turning the expansion drive shaft 136 of the inserter 12 causes expansion or contraction of the spacer 10. The drive gear 138 engages the actuation gear 24, thereby permitting adjustment of the height of the implant 10. Conversely, in the half or open positions, turning the expansion drive shaft 136 on the inserter 12 will not cause the spacer 10 to expand or contract as the lock 28 will be binding with the expansion gear 24, thereby preventing this movement. Furthermore, once the inserter 12 is removed from the implant 10, the lock 28 automatically reengages with the actuation gear 24 such that the springs 102 push the lock 28 upwards and the upper ends of guide rail posts 98 re-enter the pockets 62 in lower surface 56 of the actuation gear 24, thereby re-locking the implant 10 and preventing any further expansion or contraction of the implant 10.

Turning now to FIGS. 10-16B, an expandable interbody fusion device or implant 210 is shown according to one embodiment. The expandable implant 210 is similar to implant 10 except the locking mechanism and interaction with inserter instrument 212 has been modified, thereby allowing for three operative positions. In an unengaged state or first engagement position with inserter 212, the implant 210 is locked and prevented from expanding. In a second engagement position with inserter 212, the implant 210 is permitted to reorient for selection of a desired implantation trajectory. In a third engagement position with inserter 212, the implant 210 is permitted to expand.

Similar to implant 10, implant 210 is configured to adjust the orientation of attachment of the inserter 212 relative to the implant 210 to accommodate various surgical approaches to the spine. The ability to adjust the implantation orientation of the implant 210 accommodates a variety of approach angles and trajectories to the spine. The surgical approach angles and trajectories may include direct anterior, direct lateral, oblique, and subdivided increments in-between direct anterior and direct lateral. It will be appreciated that the surgeon may determine the best surgical approach and placement of the expandable implant 210 before or during the surgery.

Figure 11A:
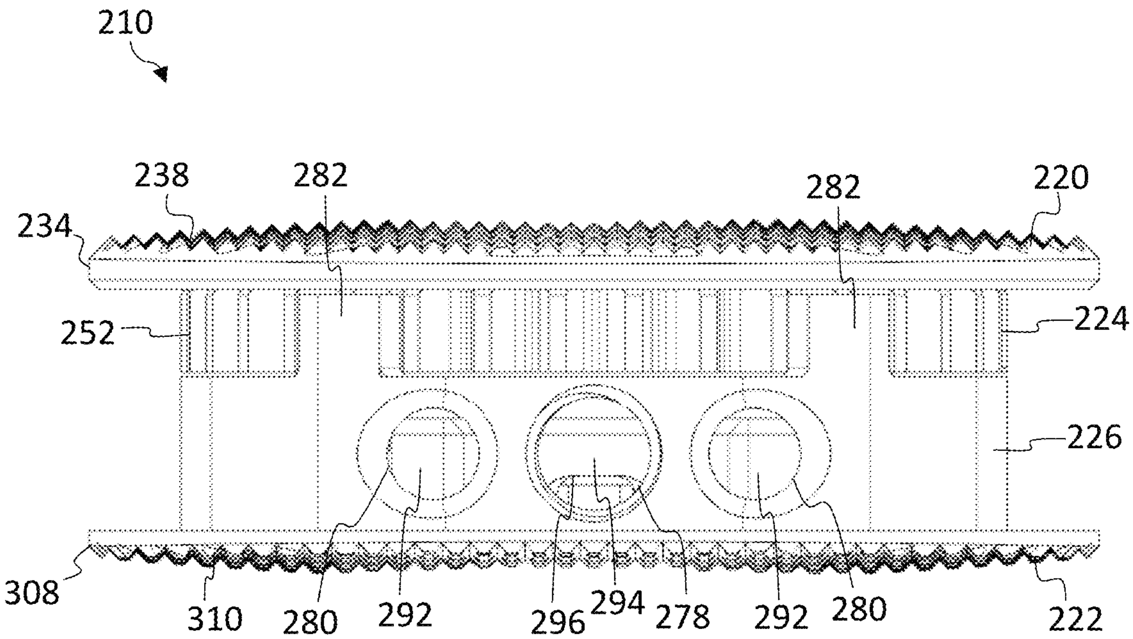
FIGS. 11A-11B show front and left side views, respectively, of the expandable fusion device of FIG. 10 at the collapsed starting height.
Figure 11B:
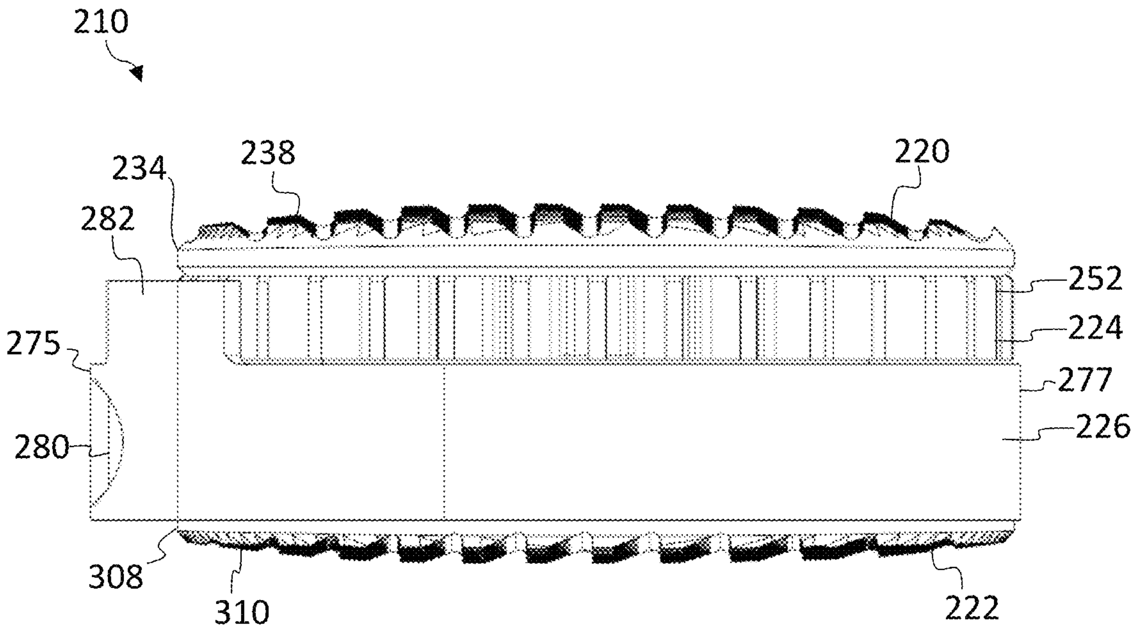
Figure 12A:
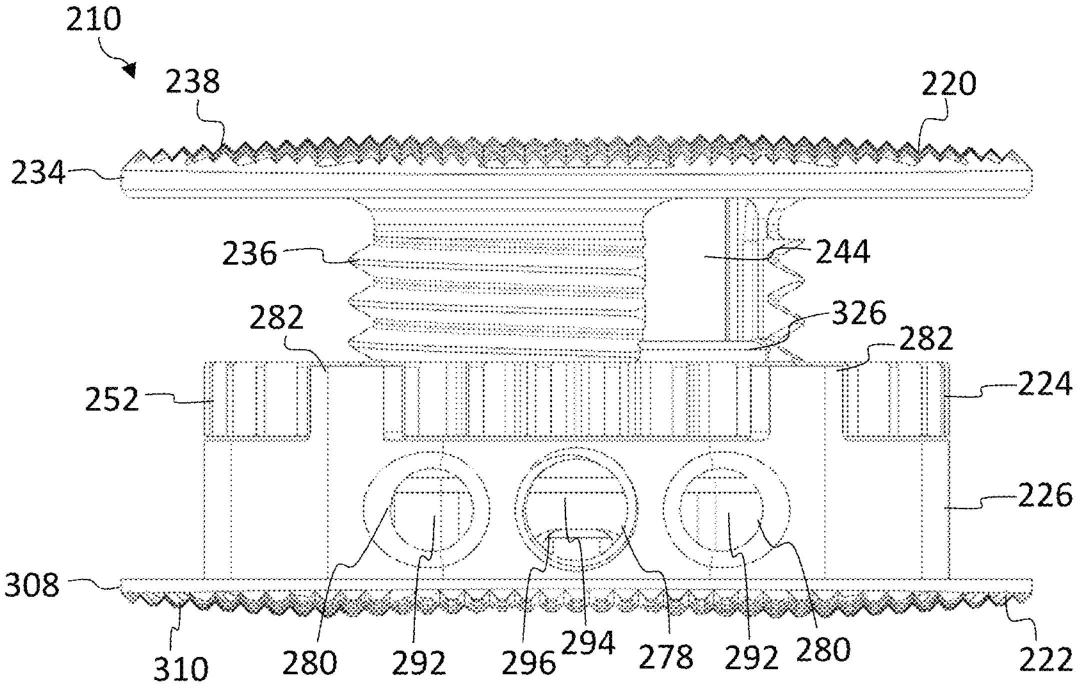
FIGS. 12A-12B show front and left views, respectively, of the expandable fusion device of FIG. 10 fully expanded in height.
Figure 12B:
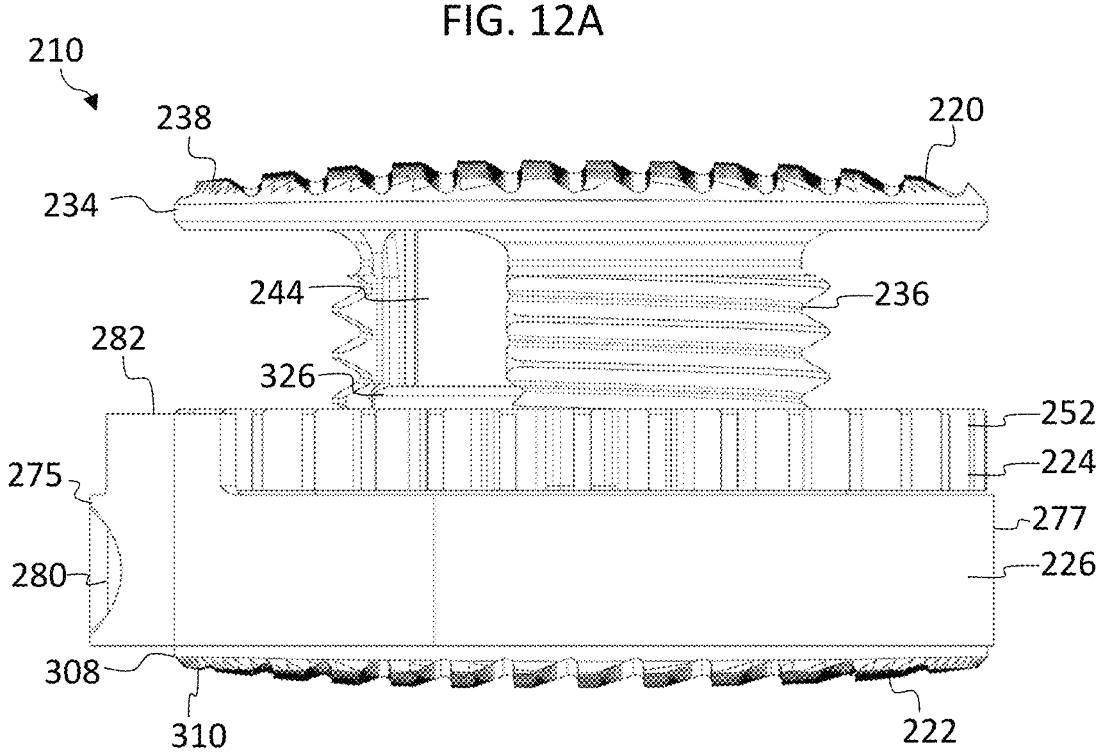

FIGS. 11A-11B show the assembled 0° implant 210 at an initial starting height in a collapsed position. Once inserted into the disc space through the desired surgical approach, the implant 210 is then expanded in height to an expanded position to precisely restore normal spinal alignment and distribute the load across the vertebral endplates 6. FIGS. 12A-12B show the assembled 0° implant 210 fully expanded. Due to the adjustable attachment interface, the implant 210 may be oriented or angled to better contact the natural endplate curvature of the vertebral bodies 4 above and below the disc space in which the device 210 is being implanted. This may be especially beneficial in high-complexity deformity cases where vertebral bodies 4 may be rotated relative to more than one dimensional plane, thus requiring a non-typical surgical access approach to the level the surgeon desires to treat.

Figure 10:
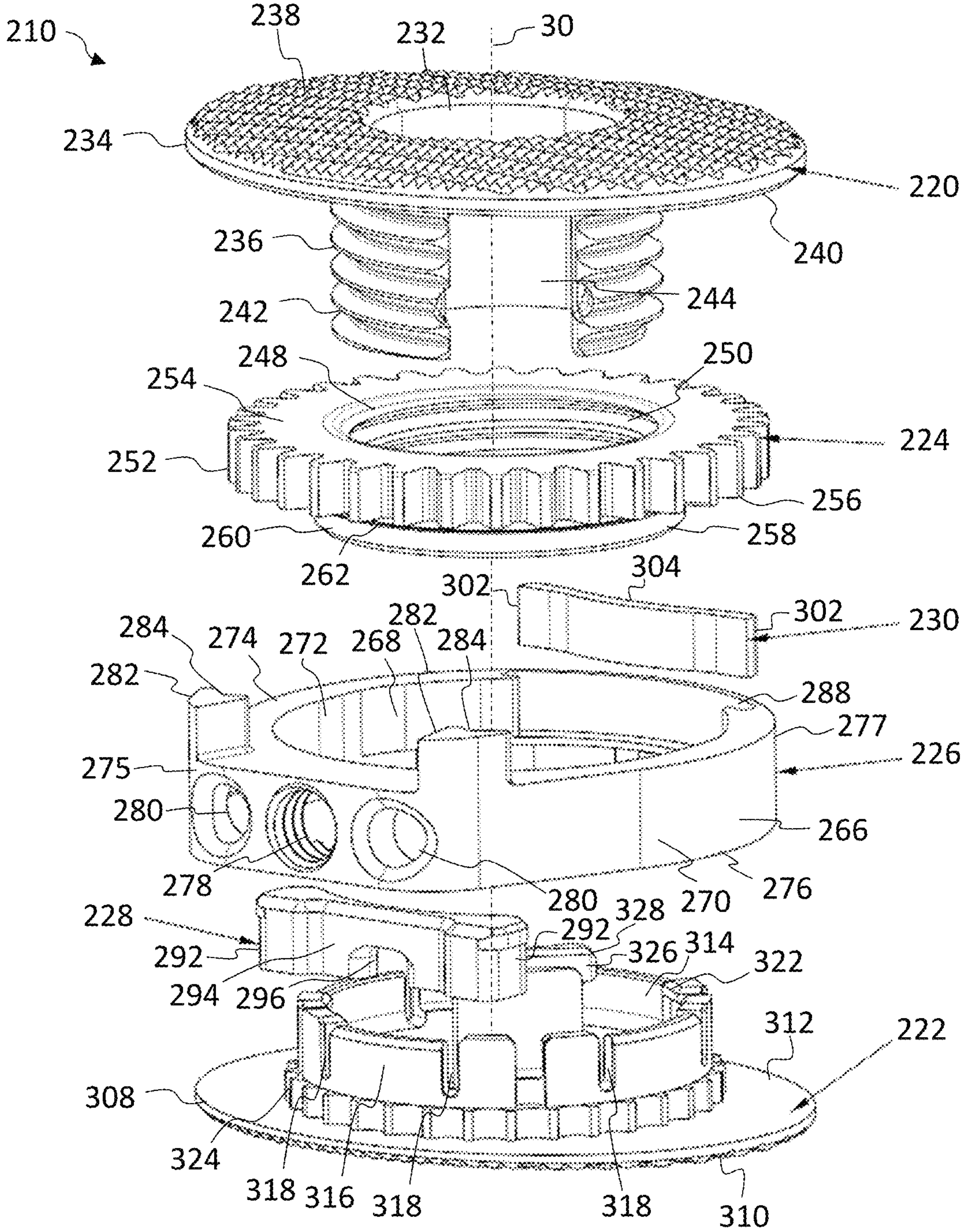
FIG. 10 is an exploded view of the expandable implant according to one embodiment.

Turning now to FIG. 10, an exploded view of expandable implant 210 is shown in more detail. The implant 210 includes an upper endplate 220 for engaging a superior vertebral body 4, a lower endplate 222 for engaging an inferior vertebral body 4, an expansion or actuation gear 224 for adjusting the height of the upper endplate 220, an interface or locking collar 226 configured to attach the inserter instrument 212 to the implant 210 at various orientations or angles for the desired surgical approach angle or trajectory, an actuation ram 228 housed in the locking collar 226 and configured to lock, unlock, or change insertion orientation of the collar 226, and a spring 230 fitted in the locking collar 226 and configured to press the locking collar 226 against the bottom endplate 222 and expansion gear 224 in the locked position. The upper and lower endplates 220, 222 and actuation gear 224 are aligned along central longitudinal axis 30. The locking collar 226 slides and moves about central longitudinal axis 30 depending on spring 230 and engagement positions with inserter 212. The implant 210 may define a large central graft retaining opening or window 232 therethrough, which is configured to receive bone graft or other suitable bone growth enhancing material.

The top or upper endplate 220 includes an annular body 234 with an inferiorly protruding cylinder 236 configured to mate with the actuation gear 224. The annular body 234 may be a ring surrounding a portion of the central graft window 232. The annular body 234 has a thickness between an upper bone-engaging surface 238 and a bottom or lower surface 240 of annular body 234. The upper bone-engaging surface 238 is configured to engage a superior vertebral body 4. The annular body 234 may be a circle, oval, ellipse, or other suitable shape for engaging the adjacent vertebral endplate 6. The upper bone-engaging surface 238 may be contoured to mimic the shape of the vertebral endplate 6 and may be provided in a variety of footprints and profiles configured to be in contact with the boney surfaces of the adjacent vertebral body. The upper bone-engaging surface 238 may include a plurality of teeth, protrusions, or other friction enhancing surfaces configured to engage bone. In one embodiment, the upper endplate 220 includes aggregate-like expulsion resistant patterns or textures on the superior surface geometry for contacting bony surfaces that can be angled to match or restore lordosis when used in the lumbar spine. The bony-contacting surface 238 may further include a porosity or porous structure to allow for additional ingrowth of bone into the spacer. The upper endplate 220 may be 3D printed, for example, to enhance boney on-growth potential. It will be appreciated that the bone-engaging surface 238 may be modified to include one or more surface treatments, coatings, textures, or other features to enhance fusion.

Cylinder 236 extends from the bottom or lower surface 240 of annular body 234. The protruding cylinder 236 defines one or more exterior threads 242 configured to mate with corresponding threads 250 inside the expansion gear 224. The exterior threads 242 may include a helical thread profile machined into the outer surface of the inferiorly protruding cylinder 236. The exterior threads 242 may have any suitable attributes including diameters, handedness, thread form, thread angle, lead(s), pitch, etc. The threads 242 may extend along the entire length of cylinder 236 or a suitable portion thereof. As the cylinder 236 is telescopingly received in/from the expansion gear 224, the upper endplate 220 is configured to raise or lower in height, thereby adjusting the overall height of the implant 210. A slot 244 may run the full length or partial length of the threads 242 and reaches into the central graft window 232. The slot 244 may be vertically oriented and in fluid communication with the central graft window 232. The slot 244 may be located at an angle, for example about 45°, from direct anterior to allow for access from various approach angles. The slot 244 may act as a backfill window and a counter-torque for expansion and collapsing of the spacer.

The expansion gear or actuation gear 224 is configured to expand and collapse the implant 210. The expansion gear 224 has a central through opening 248 sized and dimensioned to receive the protruding cylinder 236 of the upper endplate 220 in a telescoping manner. The central opening 248 has a center axis coaxial with the central longitudinal axis 30 of the implant 210. The central opening 248 defines one or more inner threads 250 cut into its inner diameter configured to interface with the exterior threads 242 of the upper endplate 220. The threaded engagement between the cylinder 236 and threaded opening 248 permit the actuation gear 224 to adjust the height of upper endplate 220 when rotated.

An outer perimeter of the expansion gear 224 includes a plurality of cogs or teeth 252. In one embodiment, the expansion gear 224 may be a spur gear or straight-cut gear with straight teeth 252 projecting radially from the cylinder or disk. The edge of each tooth 252 may be straight and aligned parallel to the axis of rotation. Although a specific arrangement of teeth 252 is shown, it is envisioned that the number, location, thickness, diameters, pitch, and configuration of the teeth may be modified or selected by one skilled in the art. When engaged by inserter instrument 212, the expansion gear 224 may be rotated about axis 30 to move upper endplate 220 up or down, thereby adjusting the height of the implant 210.

The teeth 252 may extend between an upper face 254 and an opposite lower face 256 of actuation gear 224. The upper face 254 of the expansion gear 224 may be configured to contact the bottom surface 240 of annular body 234 of the upper endplate 220 when the upper endplate 220 is fully collapsed (as shown in FIGS. 11A-11B). The lower face 256 of the expansion gear 224 is configured to contact or be adjacent to the upper surface of 274 of collar 226. The upper and lower surfaces 254, 256 of the expansion gear 224 may be generally planar and smooth.

The expansion gear 224 includes a lip 258, which protrudes inferiorly and is configured to be retained by the bottom endplate 222. The lip 258 may include a circular rim 260 defined by a circular groove 262 superior to rim 260. The circular rim 260 protrudes radially outward to engage with the bottom endplate 222. A bottom portion or surface of the rim 260 may be angled or rounded to help with a snap-fit type engagement.

The orientation and locking collar 226 is configured to interface with the inserter 212 in different states to operate the implant 210. When engaged by the inserter 212 in the first position, the collar 226 is locked against the bottom endplate 222 and the expansion gear 224, thereby fully locking the implant 210. When engaged by the inserter 212 in the second position, the slidable collar 226 is translated away from the bottom endplate 222 such that the locking collar 226 is permitted to freely spin about the central axis 30 to the desired position for implantation for a desired approach or trajectory. When engaged by the inserter 212 in the third position, the collar 226 locks against the bottom endplate 22 and is translated away from the expansion gear 224 to allow for expansion of the upper endplate 220.

Figure 13:
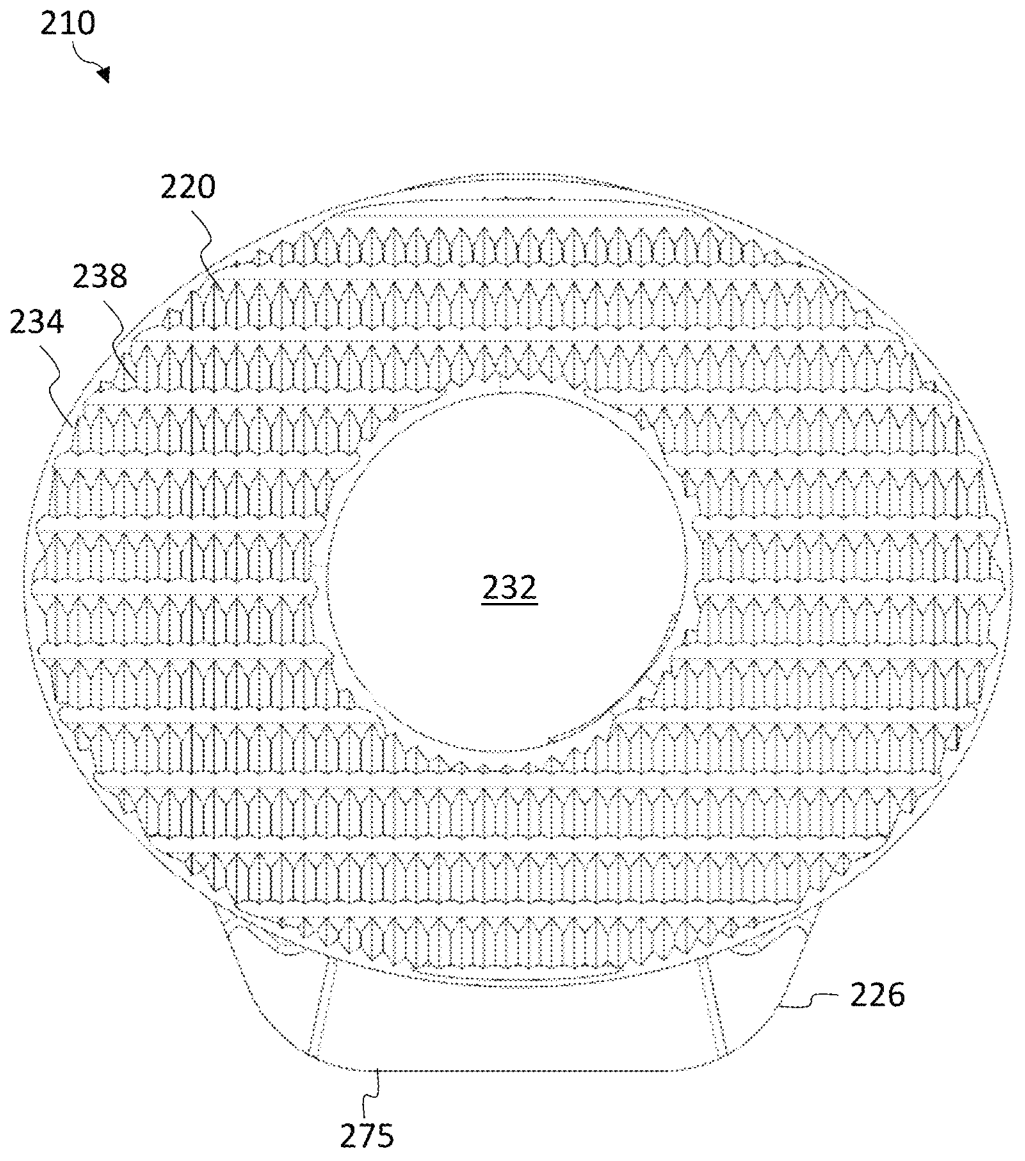
FIG. 13 shows a top view of the expandable fusion device of FIG. 10.

The locking collar 226 includes a loop or ring-shaped body 266 defining a central through opening 268 sized and dimensioned to receive a portion of lower endplate 222 and actuation gear 224. The ring-shaped body 266 has an outer face 270 and an inner face 272 with a thickness between an upper surface 274, which contacts the lower surface 256 of the expansion gear 224, and a lower surface 276, which contacts the upper surface 312 of the bottom endplate 222. Although the interface collar 226 is free to rotate about the lower endplate 222 (when in the second position), the interface collar 226 has a proximal portion 275, which always interfaces with the inserter instrument 212, and an opposite distal portion 277. As best seen in FIG. 13, the proximal portion 275 of the locking collar 226 may protrude radially past the endplates 220, 222. The proximal portion 275 may have a convex shape, for example, with a flat proximal face and rounded sides, which is sized and dimensioned to fit within a corresponding recess in the inserter instrument 212. The protruding proximal portion 275 of the collar 226 may help with alignment of the implant 210 relative to the inserter instrument 212.

The proximal portion 275 of the interface collar 226 defines one or more openings 278, 280 through the outer face 270 of the ring-shaped body 266, which are configured to interface with the inserter instrument 212 for implantation. For example, a central opening 278 may be internally threaded to interface with a threaded shaft 340 of the inserter instrument 212, and a pair of non-threaded openings 280 may be positioned on opposite sides of the central opening 278 to receive non-threaded shafts 338 of the inserter instrument 212.

The interface and locking collar 226 includes one or more vertically-projecting beams 282 extending from the upper surface 274 of the ring-shaped body 266. The vertical beams 282 may be located on the proximal portion 275 of the collar 226. For example, a pair of vertical beams 282 may be positioned on opposite sides of the instrument openings 278, 280. As best seen in FIG. 11A, in the collapsed position, the tops of each vertical beam 282 may be close to or contact the bottom surface 240 of the upper endplate 220. An inner-facing surface 284 of each beam 282 may be configured to engage with the teeth 252 of the expansion gear 224, when in the locked position. The inner-facing surface 284 may have a V-shaped cut or other suitable shape to mate with the corresponding teeth 252 on the expansion gear 224. When the locking collar 226 presses against the expansion gear 224, the inner-facing surfaces 284 of the beams 282 prevent the expansion gear 224 from turning, thereby preventing the upper endplate 220 from expanding.

The interface and locking collar 226 houses the actuation ram 228 and the spring 230. The locking collar 226 defines a pocket 286 sized and dimensioned to receive the actuation ram 228. The pocket 286 is defined into proximal portion 275 of the ring 266 from the bottom surface 276 and along the inner face 272 of the ring 266. The pocket 286 is in fluid communication with the instrument openings 278, 280, such that the actuation ram 228 is accessible to the instrument 212. The interface and locking collar 226 defines a recess 288 sized and dimensioned to receive the spring 230. The spring recess 288 may include a semi-circular cut, which mimics the curvature of the ring 266. The spring recess 288 is defined into the ring 266 from the top surface 274 and along the inner face 272 of the ring 266. The spring recess 286 may be located within the distal portion 277 of collar 226, which is opposite to the actuation ram 228 and instrument openings 278, 280.

The inner surface 272 of the locking collar 226 may include one or more mating surfaces 290 configured to interface with the teeth 324 of the bottom endplate 222 in locked configurations. The mating surfaces 290 may be located on the proximal and distal portions 275, 277, such that when the collar 226 is slid distally, the proximal portion 275 engages with the bottom endplate 222 and when the collar 226 is slid proximally, the distal portion 275 engages with the bottom endplate 222. For example, the proximal and distal mating surfaces 290 inside collar 226 may include one or more projections, edges, serrations, teeth, or the like configured to mate with the corresponding ring of teeth 324 along the top of the bottom endplate 222. The number, location, and configuration of mating surfaces 290 may be selected by one skilled in the art.

The actuation ram 228 is an intermediate component that operates within the pocket 286 and grooves cut into the locking collar 226. When the inserter 212 interfaces with the locking collar 226, the inserter 212 also interfaces with the actuation ram 228 such that the ram 228 safely presses against the bottom endplate 222 allowing the implant 210 to lock, unlock, or change insertion orientation based upon how the inserter 212 and locking collar 226 are interfacing.

The actuation ram 228 may include a body with two enlarged ends 292 with a narrowed middle section 294. The enlarged ends 292 may be generally wider than the central part 294 of the actuation ram 228. The actuation ram 228 is located inside pocket 286 in the collar 226. The enlarged ends 292 are configured to be aligned with the non-threaded openings 280 such that the enlarged ends 292 of the actuation ram 228 may be engaged by the non-threaded shafts 338 of the instrument 212. The narrowed middle section 294 defines a notch 296 configured to be partially aligned with the central threaded opening 278, which receives the threaded shaft 340 of the instrument 212. The notch 296 may define a square or rectangle with rounded corners, a squircle, or another suitable shape. The backside 298 of the actuation ram 228 is configured to contact the bottom endplate 222 to move the locking collar 226 in or out of contact with the bottom endplate 222 and expansion gear 224. The backside 298 of actuation ram 228 may be concave to interface with the rounded body of the lower endplate 222.

The spring 230 includes an elongated tab extending between opposed ends 302. The spring 230 may be bent, flexed, or deformed under force, and then return to its original shape once the force is removed. For example, the spring 230 may include a curved or arched central section 304, which can flexibly deform under pressure. The ends 230 of the spring 230 fit within the ends of spring recess 288 in the locking collar 226. In its relaxed state and in the first inserter position (shown in FIG. 14A), the curved central section 304 protrudes from recess 288 such that the spring 230 forces collar 226 against the bottom endplate 222 and expansion gear 224. In the second inserter position (shown in FIG. 15A), the curved central section 304 still protrudes from recess 288 but the locking collar 226 is pressed away from the teeth 324 of the bottom endplate 222 such that the locking collar 226 is permitted to freely spin around the implant 210. In the third inserter position (shown in FIG. 16A), when enough force is applied to overcome the spring's resistance, the spring 230 is overpowered such that the curved central section 304 inverts or flips past its equilibrium and fully seats into the spring recess 288 in the locking collar 226. Once this force is removed, the spring 230 rebounds to its relaxed state (shown in FIG. 14A).

The bottom or lower endplate 222 includes an annular body 308, which may be a ring surrounding a portion of central graft window 232. The annular body 308 has a thickness between a lower bone-engaging surface 310 and an upper surface 312 of annular body 308. The annular body 308 may be angled and/or the thickness between the upper and lower surfaces 310, 312 of the annular body 308 may vary to accommodate wide ranging anatomical profiles and to match or restore lordosis when used in the lumbar spine.

The lower bone-engaging surface 310 of lower endplate 222 is configured to engage an inferior vertebral body 4. The lower bone-engaging surface 310 may be contoured to mimic the shape of the vertebral endplate 6 and may be provided in a variety of footprints and profiles configured to be in contact with the boney surfaces of the adjacent vertebral body. Similar to upper bone-engaging surface 238, lower bone-engaging surface 310 may include a plurality of teeth, protrusions, or other friction enhancing surfaces configured to engage bone. In one embodiment, the bottom endplate 222 includes aggregate-like expulsion resistant patterns or textures on the inferior surface geometry for contacting bony surfaces that can be angled to match or restore lordosis when used in the lumbar spine. The lower bone-engaging surface 310 may further include a porosity or porous structure to allow for additional ingrowth of bone into the spacer. The lower endplate 222 may be 3D printed, for example, to enhance boney on-growth potential. It will be appreciated that the bone-engaging surface 310 may be modified to include one or more surface treatments, coatings, textures, expulsion resistant structures or geometries, or other features to enhance fusion.

Assembly, counter-torque, and interfacing features for the locking collar 226 and expansion gear 224 are machined into an upper portion of the lower endplate 222. The locking collar 226 nests between the actuation gear 224 and the bottom endplate 222. The bottom 276 of locking collar 226 is close to or contacts upper surface 312 of the annular body 308. The lower endplate 222 has an inner wall 314 defined by a portion of central graft window 232 and an outer wall 316. A plurality of slits 318 extend vertically between the inner and outer walls 314, 316. As best seen in FIG. 14B, the inner wall 314 defines a recess 320 configured to fit circular rim 260 and an overhang or finger 322 configured to fit in the groove 262 of expansion gear 224. The fingers 322 may be configured to flex or bend slightly as the fingers 322 are inserted into groove 262, thereby securely connecting the expansion gear 224 to the lower endplate 222.

A ring of teeth 324 may be provided on the bottom endplate 222 to engage with the locking collar 226 in certain positions. The ring of teeth 324 may be located between the outer wall 314 and the upper surface 312 of the annular body 308. The ring of teeth 324 may include straight teeth projecting radially from the outer wall 314. The edge of each tooth 324 may be straight and aligned parallel to the axis of rotation. The apex of each tooth 324 may be truncated and the space between each tooth 324 may be rounded or semi-circular, for example. Although a specific arrangement of teeth 324 is shown, it is envisioned that the number, location, thickness, diameters, pitch, and configuration of the teeth may be modified or selected by one skilled in the art. When the mating teeth 290 on the locking collar 226 engage with teeth 324, the locking collar 226 is locked relative to the bottom endplate 222. When disengaged from teeth 324, the locking collar 226 is free to rotate to the desired implantation orientation.

The lower endplate 222 may include a pillar 326, which may be sized and dimensioned to fit within slot 244 in the cylinder 236 of the upper endplate 220. The pillar 326 may protrude vertically from the upper surface 312 of the lower endplate 222. The pillar 326 may include a horizontal beam 328 with opposing ends that fit into corresponding grooves in the cylinder 236 of the upper endplate 220. An inner facing surface 330 may be curved to mimic the shape of the central graft window 232. When expansion gear 224 is rotated to expand the upper endplate 220, the slot 244 and pillar 326 act as a counter-torque measure when expanding and collapsing the upper endplate 220.

Turning now to FIGS. 14A-16B, implant 210 is insertable into the disc space with inserter 212 through an agnostic approach. In other words, the surgeon is able to determine the trajectory or approach to the spine before or during the procedure and is able to adjust the orientation of the implant 210 during the procedure to accommodate the desired surgical approach. The surgical approach angles and trajectories may include direct anterior, direct lateral, oblique, and chosen locations in-between direct anterior and direct lateral. In some cases, the implant 210 may help to resolve insufficient anterior-posterior distance of the intervertebral disc space during the insertion and placement of wider medial-lateral footprint spacers from an anterior-to-psoas approach. In addition, the implants 210 may be inserted from multiple approaches without the need for an extensive set of implants with fixed approach-specific insertion features. The ability to be inserted from multiple approaches and trajectories significantly reduces the number of necessary implants in the set for a given procedure. The flexibility of implant 210 also provides the surgeon with more choices and greater control during the procedure, thereby resulting in better patient outcomes.

The inserter 212 controls the position and orientation of the interface collar 226 and the expanded height of the top endplate 220 when properly attached. The inserter 212 includes a distal end 332 configured to attach to the interface collar 226 of the implant 210. The inserter 212 may include a main outer body 334 in the form of a hollow outer tube or cannula, which may include an expansion assembly and an attachment assembly. The attachment assembly may include a distal attachment interface 336 sized to receive the proximal portion 275 of the locking collar 226, a pair of non-threaded shafts 338 configured to engage non-threaded openings 280, and a central threaded shaft 340 configured to engage threaded opening 278 in the locking collar 226.

Figure 14A:
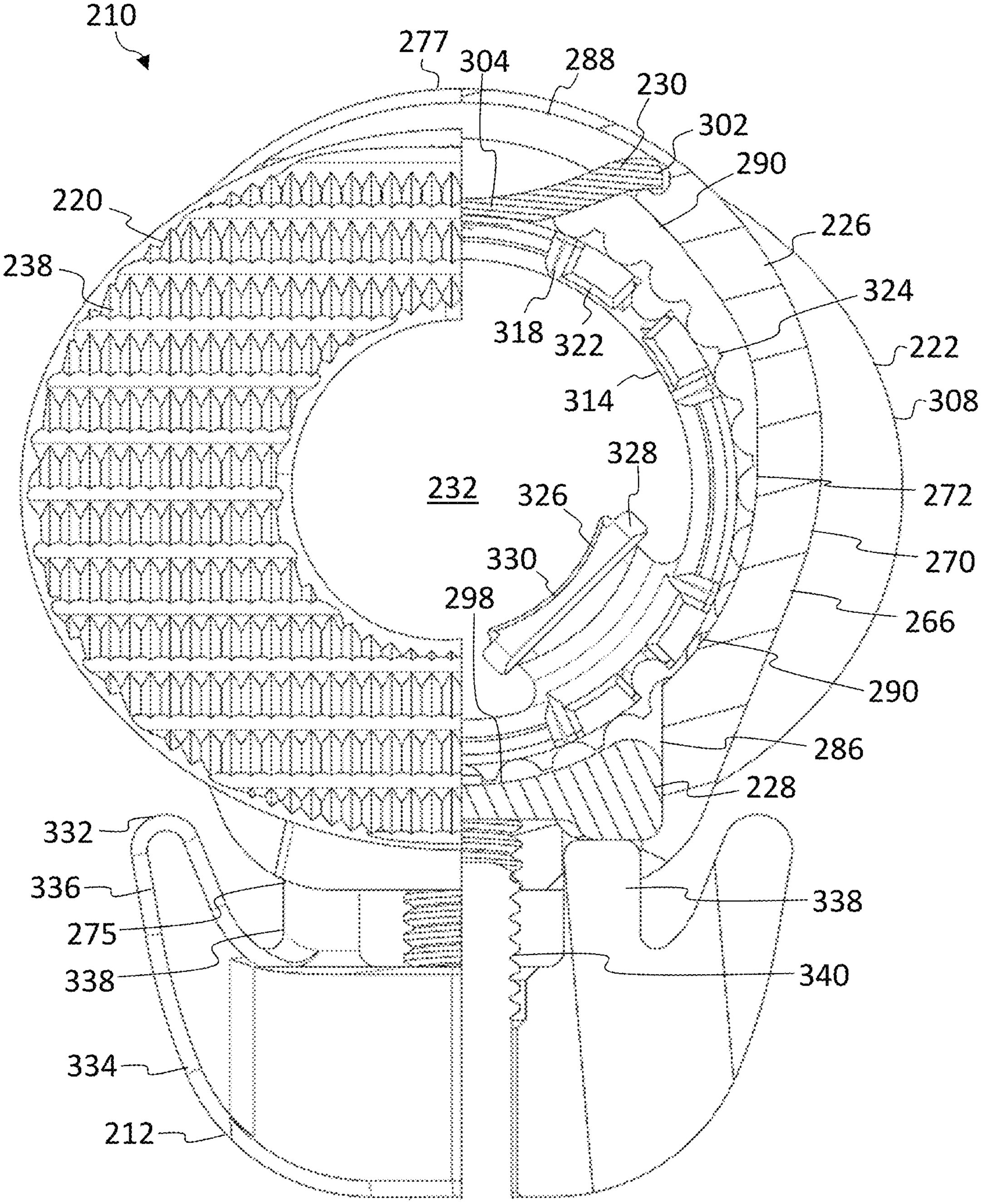
FIGS. 14A-14B show a partial top view (left side) and a partial cross-sectional view (right side) and a side cross-sectional view, respectively, of the inserter instrument engaged with the implant at a first position with the expansion mechanism fully locked by the collar.
Figure 14B:
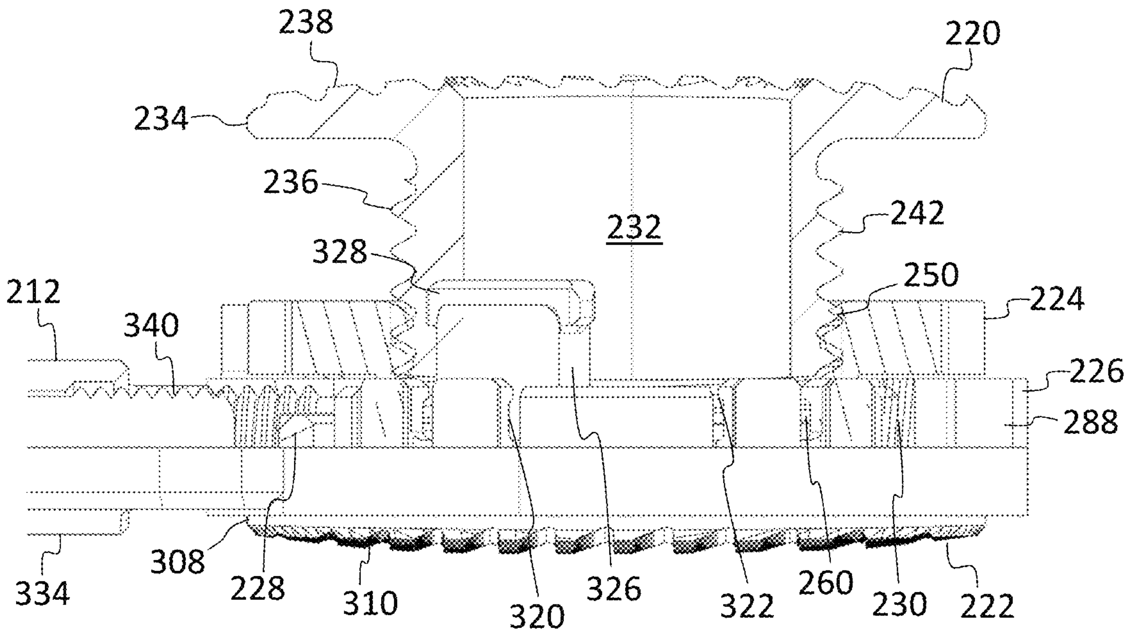

FIGS. 14A-14B show inserter instrument 212 attached to implant 210 in a first position. In the first position or unengaged state, the implant 210 is locked such that the collar 226 and the expansion gear 224 are fully locked. The non-threaded shafts 338 may be received in openings 280, but the shafts 338 do not apply any force to actuation ram 228. In this position, the inserter 212 is not threaded into the locking collar 226 in any capacity. Protruding interfacing geometry of the inserter 212 may be touching or guiding the inserter 212 to the correct aligning position to thread into the locking collar 226. Mating, binding and/or interfering geometry on the proximal portion 275 of locking collar 226 engages with similar complimentary interfacing surfaces on the bottom endplate 222 as the spring 230 pulls/pushes against the locking collar 226 and bottom endplate 222.

In the first position, the locking collar 226 locks to the bottom endplate 222 and the expansion gear 224. The spring 230 of locking collar 226 presses the locking collar 226 against the bottom endplate 222 and expansion gear 224 simultaneously. The spring 230 forces locking collar 226 in a distal direction away from the inserter 212. In this first position, the mating surfaces 290 of the locking collar 226 interface with the teeth 324 of the bottom endplate 222, thereby acting as a counter-torque and preventing the locking collar 226 from rotating. The contacting surfaces 284 on the beams 282 also interfere with the teeth 252 on the expansion gear 224, which interferes with the rotational movement of the expansion gear 224 and prevents both expansion and collapse of the implant 210.

Figure 15A:
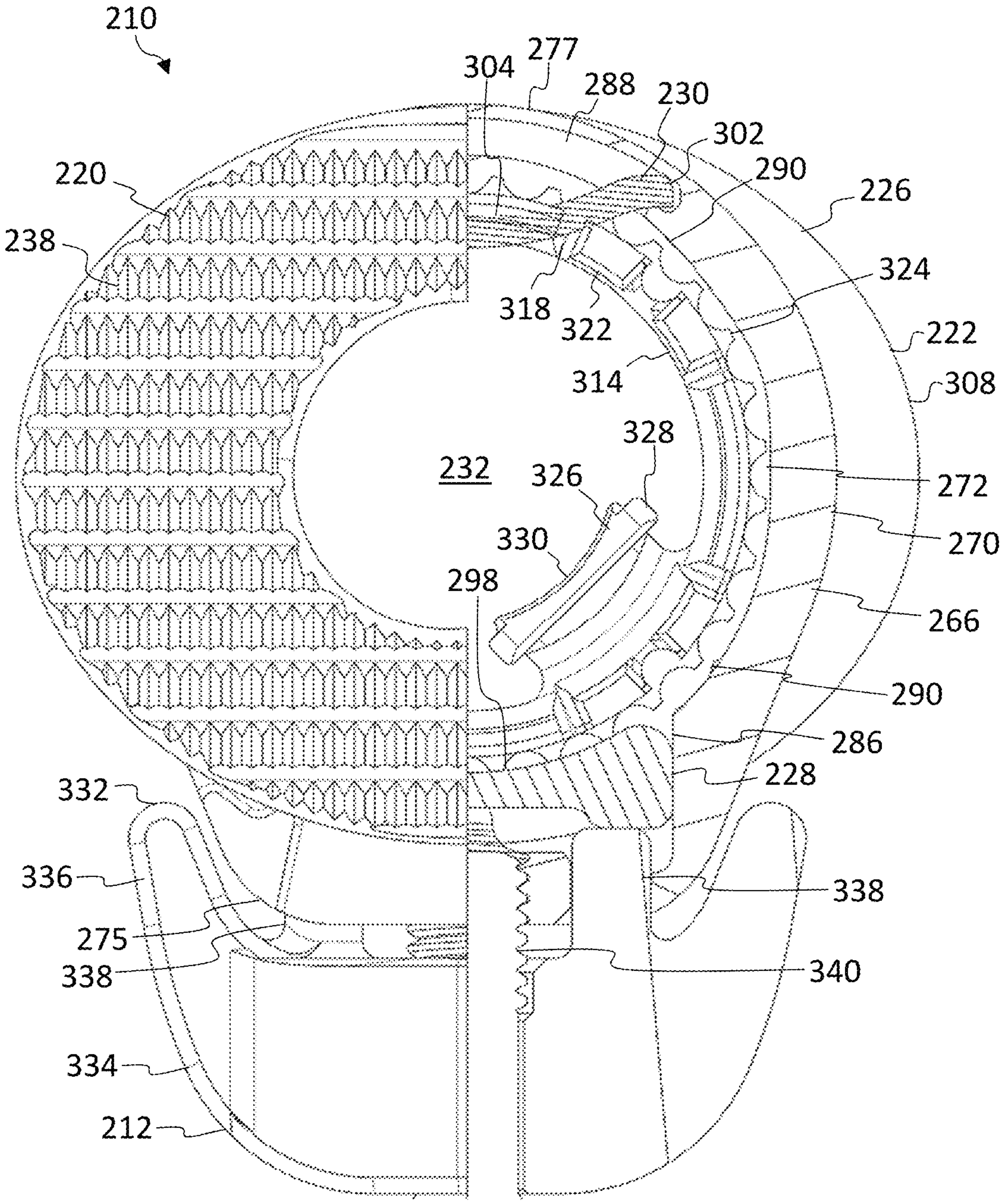
FIGS. 15A-15B show a partial top view (left side) and a partial cross-sectional view (right side) and a side cross-sectional view, respectively, of the inserter instrument engaged with the implant at a second position where the collar is permitted to freely rotate to select the insertion orientation.
Figure 15B:
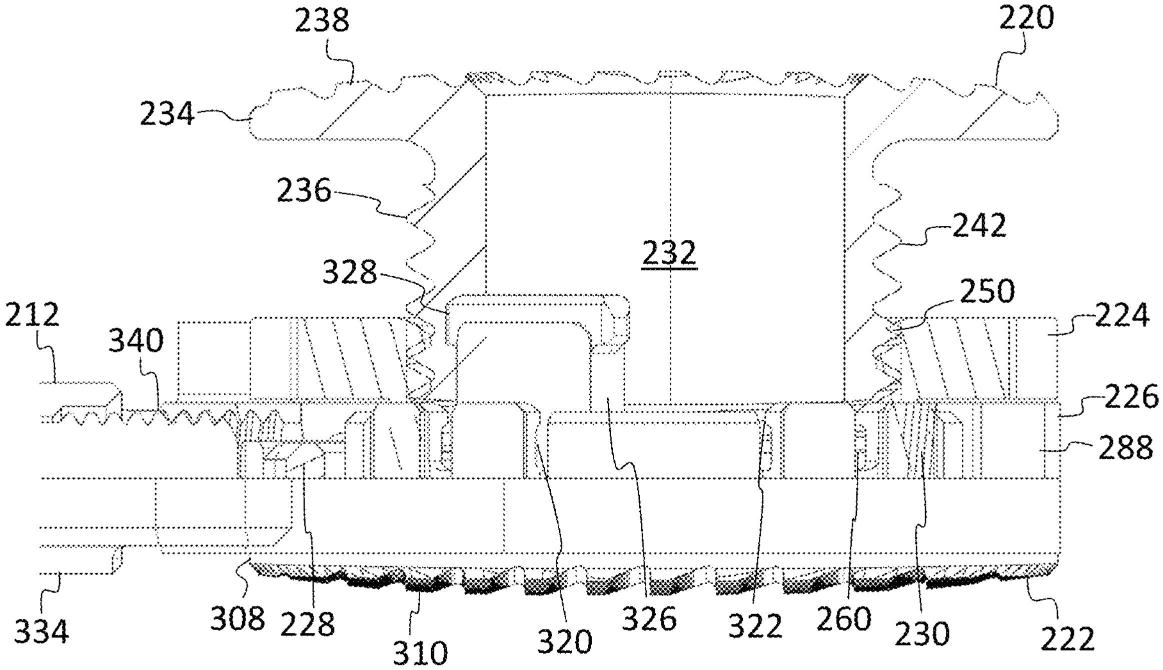

FIGS. 15A-15B show inserter instrument 212 attached to implant 210 in a second position. In the second position, the locking collar 226 can only move, by rotating about the lower endplate 222, when the inserter 212 is correctly attached. In this position, the locking collar 226 is permitted to rotate to the desired insertion orientation but the expansion gear 224 is still locked. The non-threaded and threaded shafts 338, 340 may be received in openings 278, 280 such that the shafts 338, 340 apply a force to the actuation ram 228, which moves the locking collar 226 toward the instrument 212. In the second position, the inserter 212 is threaded into the locking collar 226 to a pre-determined position but not fully threaded into the collar 226.

The protruding interfacing geometry of the inserter 212 is configured to touch the implant 210 and helps to control the orientation of the implant 210 relative to the inserter 212 for implantation. The actuation ram 228 presses against the central elements of the bottom endplate 222 such that the locking collar 226 is pulled and translated by the threaded engagement 340 of the inserter 212, moving all mating, binding, and/or interfering geometry away from the bottom endplate 222 and the expansion gear 224. When engaged with the inserter 212 at the second position, the locking collar 226 is pressed away from the interfacing teeth 324 on the bottom endplate 222 and held in this position by the spring 230. The locking collar 226 is permitted to freely spin around the implant 210 to apply a desired inserter-to-implant orientation for implantation.

Figure 16A:
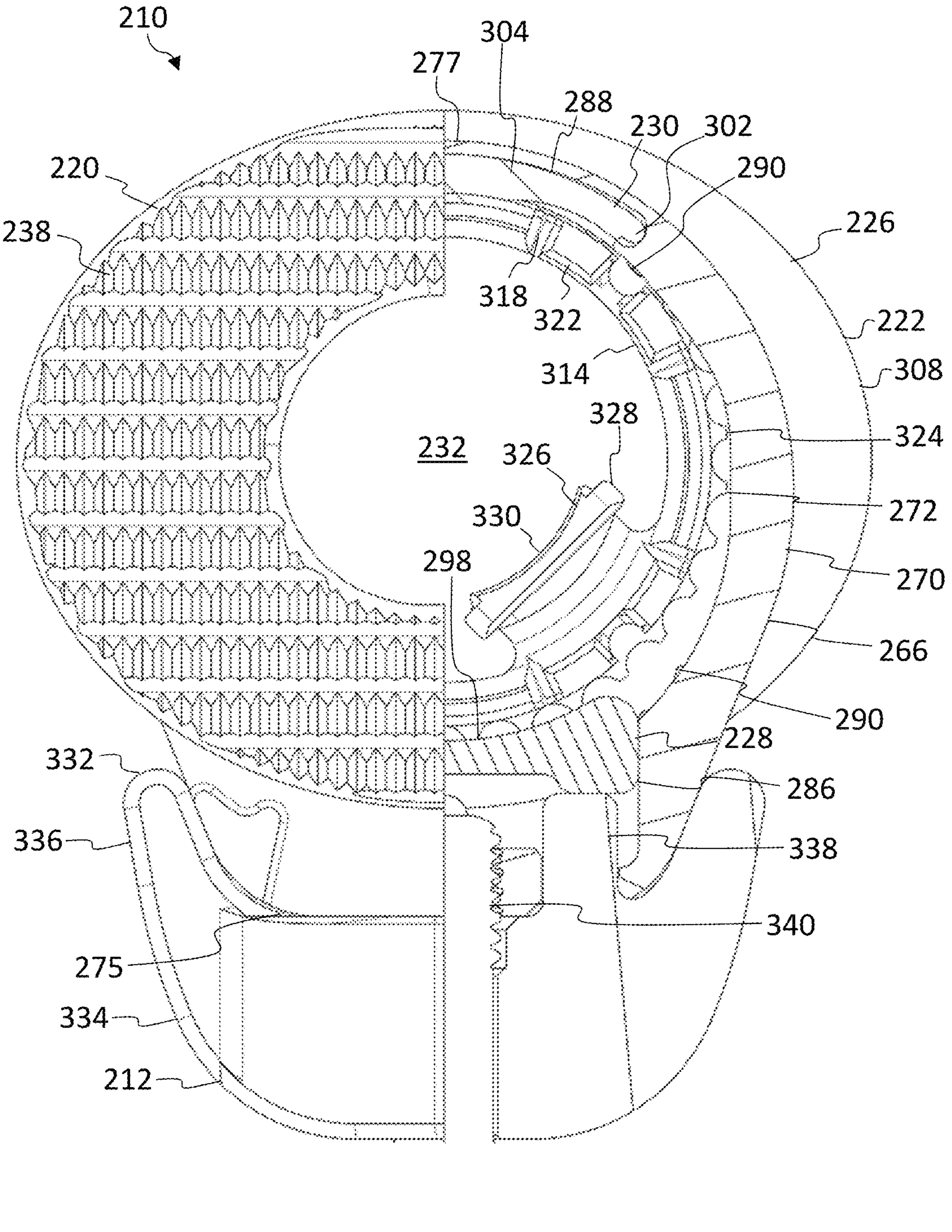
FIGS. 16A-16B show a partial top view (left side) and a partial cross-sectional view (right side) and a side cross-sectional view, respectively, of the inserter instrument engaged with the implant at a third position where the collar is not permitted to rotate and the expansion gear is able to expand or contract the implant.
Figure 16B:
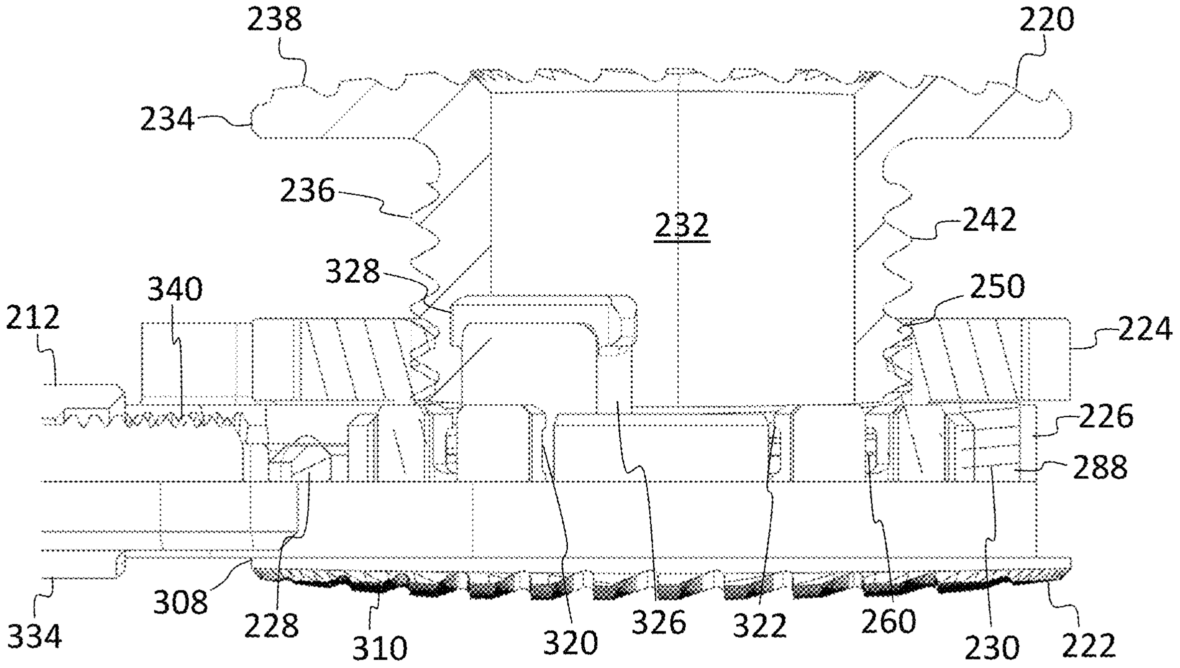

FIGS. 16A-16B show inserter instrument 212 attached to implant 210 in a third position. In the third position, the locking collar 226 is locked relative to the bottom endplate 222, but the expansion gear 226 is released and free to rotate to expand the upper endplate 220. The non-threaded and threaded shafts 338, 340 may be received in openings 278, 280 such that the shafts 338, 340 apply a force to the actuation ram 228, which moves the locking collar 226 fully into instrument 212. When the inserter 212 is threaded into the locking collar 226 fully such that the actuation ram 228 presses against the central elements of the bottom endplate 222, the locking collar 226 is pulled and translated by the threaded engagement of the inserter 212 pulling the mating, binding and/or interfering geometry on the distal portion 277 of locking collar 226 into similar complimentary interfacing surfaces 324 on the bottom endplate 222. In the third position, the inserter 212 is able to drive expansion or contraction of the implant 210 by actuating the expansion gear 224.

When engaged with the inserter 212 at this third position, the actuation ram 228 is fully pressed against the bottom endplate 222 and the locking collar 226 is pulled tight against the bottom endplate 222, fully overpowering the spring 230. The spring 230 flips into the spring recess 288 in the locking collar 226. The patterned mating surfaces 290 on the locking collar 226 engage with the teeth 324 on bottom endplate to set the orientation of the inserter 212 to the implant 210 and ready the implant 210 for surgical insertion. In the third position, the combined interfacing geometry of the bottom endplate 222, actuation ram 228, and the locking collar 226 rigidly orients the implant 210 to the inserter 212 and can be implanted at the determined orientation. The third position also unlocks the expansion gear 226 through disengaging the interfacing geometry 284 on the top of the locking collar 226 by pulling the locking collar 226 proximally toward the inserter 212 and away from the expansion gear 224. In this state, the implant 210 may be expanded or contracted when the expansion gear 224 is articulated by the inserter 212.

In one embodiment, robotic and/or navigation guidance may be used to assist in orienting and installing the implants 10, 210 along one or more of the agnostic approaches. Details of surgical robotic and/or navigation systems can be found, for example, in U.S. Pat. Nos. 10,675,094 and 9,782,229, which are incorporated by reference herein in their entireties for all purposes. The implant 10 may be implanted with one or more of the following steps: (1) determining optimal implant location and positioning to optimize contacted bone and desired correction; (2) employing robotic and/or navigational systems to determine the potential trajectories to allow for optimal implant location and outcome; (3) optionally docking a cannula on the disc space through a suitable trajectory including direct anterior, direct lateral, or a non-specified oblique approach between anterior and lateral; (4) inserting the expandable interbody 10 into the disc space in a collapsed position through the given trajectory; and (5) expanding the expandable interbody 10 in height to precisely restore disc height and spinal alignment (e.g., lordosis).

The implant and systems described herein may include one or more of the following advantages: (1) the ability to adjust the orientation of attachment to the implant to accommodate various approaches; (2) an internal automatic lock that both provides discrete orientation positions about the central axis of the implant and automatically locks the device after insertion into the disc space; and (3) the ability to expand in height when implanted to achieve a desired spacer height which in turn provides a desired disc height.

The ability to adjust the implantation orientation of the spacer relative to the spacer's sagittal angle accommodates a variety of approach angles and trajectories which include, but are not limited to, direct anterior, direct lateral, oblique, and subdivided increments in-between direct anterior and direct lateral. The spacer has a retained interfacing collar which can freely rotate about the device's central axis. By pivoting/rotating about the central axis, the device can be oriented to better interface with the natural endplate curvature of the vertebral bodies above and below the disc space in which the device is being implanted. This may be especially beneficial in high-complexity deformity cases where vertebral bodies may be rotated relative to more than one dimensional plane, thus requiring a non-typical surgical access approach to the level the surgeon desires to treat.

The automatic lock with discrete orientation positions provides two functions of both automatically locking the implant preventing expansion and collapsing of the implant, and discretely orienting the implant on the inserter for implantation. The automatic lock function reduces the steps intraoperatively needed to successfully implant the device potentially reducing cognitive load on the surgeon and making for a safer overall procedure as the step to lock the implant cannot be forgotten by the surgeon. The discrete orientations the lock provides allow the surgeon to adapt to the approach that best fits the patient's anatomy.

Unlike static spacers that only provide height restoration at discrete intervals, the expandable implant is inserted into the intervertebral disc space at a collapsed height and then expand axially to restore height loss in the disc space. The ability to expand in height when implanted allows for the surgeon to restore collapsed disc height at any height from the implant starting height up to and including the fully expanded height. In addition, the expandable interbody spacer maximizes volume within and around the device for graft material.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:

an upper endplate and a lower endplate configured to engage adjacent vertebrae;

an expansion gear configured to adjust a height of the upper endplate, the expansion gear is coupled to the lower endplate and engaged with the upper endplate;

a locking collar positioned between the expansion gear and the lower endplate and configured to attach to an inserter instrument at multiple orientations for a desired surgical approach;

an actuation ram housed in the locking collar configured to lock, unlock, or change insertion orientation of the locking collar; and a robotic and/or navigational system configured to determine desired trajectories to allow for the positioning and expansion of the expandable implant.

2. The expandable implant of claim 1, wherein in a first position, the locking collar is locked against the lower endplate and the expansion gear, thereby fully locking the implant, wherein in a second position, the locking collar is permitted to freely spin about the lower endplate for the desired surgical approach, and wherein in a third position, the locking collar locks against the lower endplate and is translated away from the expansion gear, thereby allowing for expansion of the upper endplate.

3. The expandable implant of claim 1, wherein the lower endplate includes a ring of teeth configured to interface with corresponding mating surfaces in the locking collar.

4. The expandable implant of claim 1, wherein a spring is an elongated tab with a curved central section, which deforms under force.

5. The expandable implant of claim 1, wherein the actuation ram includes a body with two enlarged ends with a narrowed middle section.

6. The expandable implant of claim 1, wherein a spring is received in a recess in the locking collar and the spring is located opposite to the actuation ram.

7. The expandable implant of claim 1, wherein the expansion gear includes a disk with a plurality of teeth projecting radially outward therefrom and a threaded central opening configured to threadedly mate with the upper endplate.

8. The expandable implant of claim 7, wherein the locking collar includes a pair of vertically projecting beams each having an inner-facing surface configured to engage with the teeth of the expansion gear.

9. The expandable implant of claim 1, wherein the upper endplate includes an annular body with a bone-engaging surface and an inferiorly protruding cylinder configured to mate with the expansion gear, wherein the inferiorly protruding cylinder of the upper endplate includes exterior threads and a vertical slot bisecting the exterior threads, and the lower endplate includes a pillar receivable in the vertical slot.

10. An implantable system comprising:

an expandable implant comprising an upper endplate configured to engage a superior vertebra, a lower endplate configured to engage an inferior vertebra, an expansion gear configured to adjust a height of the upper endplate, a locking collar configured to rotate about the lower endplate for a desired surgical approach, a spring for biasing the locking collar toward or away from the lower endplate and the expansion gear, and an actuation ram housed in the locking collar configured to lock, unlock, or change insertion orientation of the locking collar; and an inserter instrument having an attachment assembly configured to engage the locking collar and an expansion assembly configured to expand the implant, wherein the inserter instrument is attachable to the locking collar in a first position for fully locking the implant, a second position permitting the locking collar to freely spin for the desired surgical approach, and a third position allowing for expansion of the upper endplate, a navigation guidance system configured to assist in orienting and installing the expandable implant along one or more trajectories.

11. The implantable system of claim 10, wherein the locking collar includes a central opening, which is internally threaded, and a pair of openings positioned on opposite sides of the central opening, which are non-threaded.

12. The implantable system of claim 11, wherein the actuation ram is located inside a pocket in the locking collar, the actuation ram includes a body with two enlarged ends and a narrowed middle section, wherein the two enlarged ends are aligned with the the pair of openings and the narrowed middle section is aligned with the central opening.

13. The implantable system of claim 12, wherein the narrowed middle section defines a notch partially aligned with the central opening.

14. The implantable system of claim 12, wherein the inserter instrument includes a central threaded shaft configured to engage the central opening, and a pair of non-threaded shafts configured to engage the pair of openings.

15. The implantable system of claim 14, wherein in the first position, the inserter instrument is attached to the implant such that the inserter instrument is not threaded into the locking collar, the spring biases the locking collar against the lower endplate and the expansion gear, thereby fully locking the implant.

16. The implantable system of claim 14, wherein in the second position, the inserter instrument is attached to the implant such that the inserter instrument is threaded into the locking collar to a pre-determined position, the non-threaded shafts push against the actuation ram, and the locking collar releases from the lower endplate, thereby permitting the locking collar to freely spin for the desired surgical approach.

17. The implantable system of claim 14, wherein in the third position, the inserter instrument is attached to the implant such that the inserter instrument is fully threaded into the locking collar, the non-threaded shafts push against the actuation ram overpowering the spring, and the locking collar releases the expansion gear, thereby allowing for expansion of the upper endplate.

18. A method of installing an expandable implant comprising:

providing an expandable implant having an upper endplate, a lower endplate, an expansion gear configured to adjust a height of the upper endplate, a locking collar configured to rotate about the lower endplate for a desired surgical approach, and an actuation ram housed in the locking collar configured to lock, unlock, or change insertion orientation of the locking collar;

employing robotic and/or navigational systems to determine potential trajectories to allow for optimal expandable implant location;

providing an inserter instrument;

controlling the position and orientation of the locking collar through the inserter instrument to determine a desired trajectory;

docking a cannula on a disc space through the desired suitable trajectory including direct anterior, direct lateral, or a non-specified oblique approach between anterior and lateral;

inserting the expandable implant into the disc space in a collapsed position through the desired trajectory with the inserter instrument; and expanding the expandable implant in height to precisely restore disc height and spinal alignment.

19. The method of claim 18, wherein in an unengaged state, the implant is locked such that the locking collar and the expansion gear are fully locked.

20. The method of claim 18, wherein the desired trajectory is selected from the direct anterior, the direct lateral, or the non-specified oblique approach between the direct anterior and the direct lateral.

* * * * *